US012569682B2

(12) United States Patent
Libbus et al.

(10) Patent No.: US 12,569,682 B2
(45) Date of Patent: Mar. 10, 2026

(54) AUTOMATIC TITRATION WITH DEFIBRILLATION SENSITIVITY COMPENSATION

(71) Applicant: LivaNova USA, Inc., Houston, TX (US)

(72) Inventors: Imad Libbus, St. Paul, MN (US); Scott Stubbs, Maple Grove, MN (US); Bruce KenKnight, Maple Grove, MN (US)

(73) Assignee: LivaNova USA, Inc., Houston, TX (US)

( * ) Notice: Subject to any disclaimer, the term of this patent is extended or adjusted under 35 U.S.C. 154(b) by 346 days.

(21) Appl. No.: 18/135,325

(22) Filed: Apr. 17, 2023

(65) Prior Publication Data

US 2024/0342479 A1 Oct. 17, 2024

(51) Int. Cl.
*A61N 1/36* (2006.01)
*A61B 5/335* (2021.01)

(52) U.S. Cl.
CPC .......... *A61N 1/36114* (2013.01); *A61B 5/335* (2021.01); *A61N 1/36139* (2013.01)

(58) Field of Classification Search
CPC . A61N 1/36114; A61N 1/36139; A61B 5/335
USPC .......................................................... 607/9
See application file for complete search history.

(56) References Cited

U.S. PATENT DOCUMENTS 5,403,355 A * 4/1995 Alt ..................... A61N 1/39622
607/9

* cited by examiner

*Primary Examiner* — Nadia A Mahmood
(74) *Attorney, Agent, or Firm* — Foley & Lardner LLP

(57) ABSTRACT

A method of delivering neurostimulation therapy to a patient from an implantable medical device is provided. The method includes delivering, by the implantable medical device, the neurostimulation therapy to the patient. The method further includes determining, by the implantable medical device, that the patient has received a defibrillation shock from a defibrillation device. The method further includes adjusting, by the implantable medical device, the neurostimulation therapy based on determining that the patient has received the defibrillation shock.

20 Claims, 8 Drawing Sheets

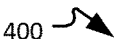
400
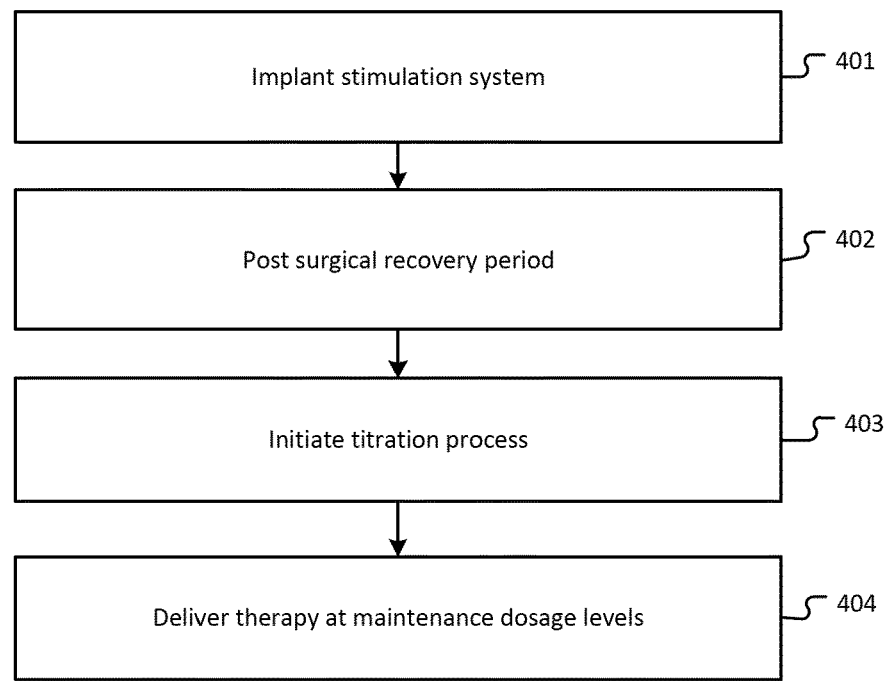
| Implant stimulation system | 401 |
| Post surgical recovery period | 402 |
| Initiate titration process | 403 |
| Deliver therapy at maintenance dosage levels | 404 |
FIG. 5
500
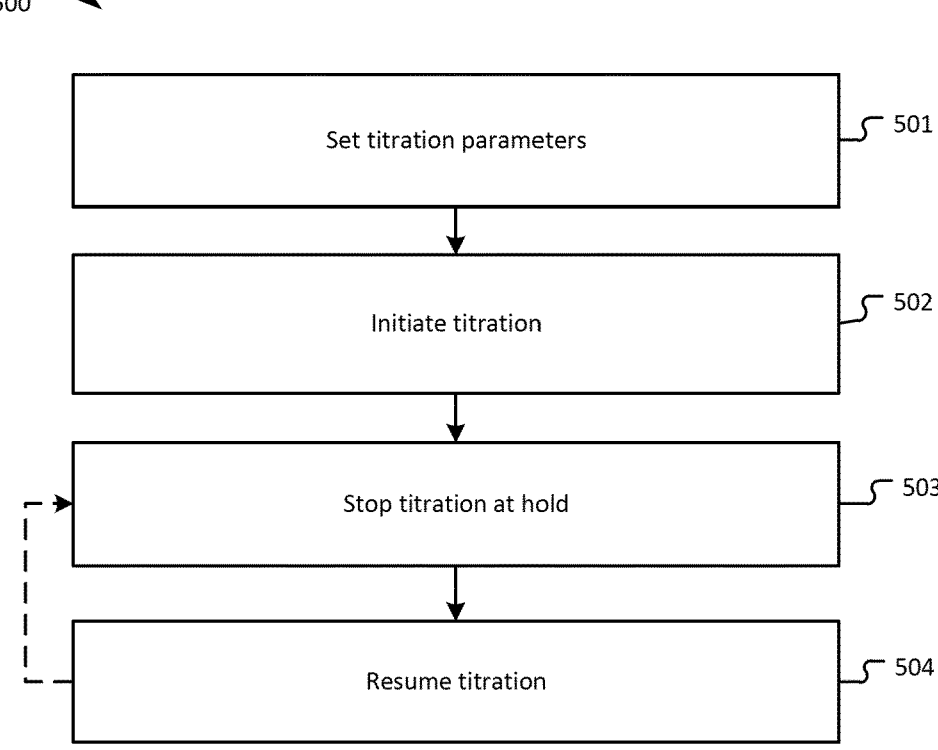
| Set titration parameters | 501 |
| Initiate titration | 502 |
| Stop titration at hold | 503 |
| Resume titration | 504 |
FIG. 6A

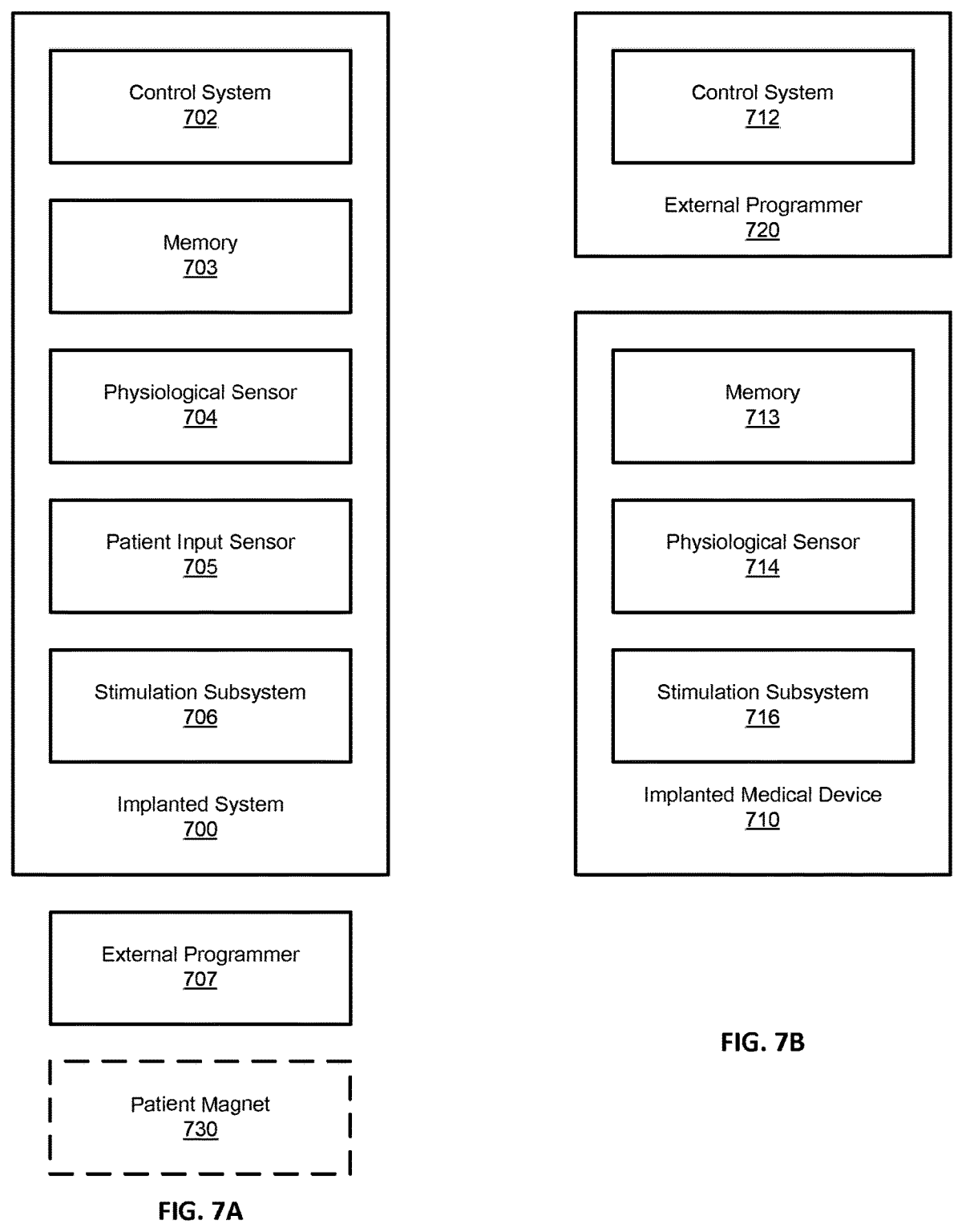

Control System
702

Memory
703

Physiological Sensor
704

Patient Input Sensor
705

Stimulation Subsystem
706

Implanted System
700

External Programmer
707

Patient Magnet
730

FIG. 7A

Control System
712

External Programmer
720

Memory
713

Physiological Sensor
714

Stimulation Subsystem
716

Implanted Medical Device
710

FIG. 7B

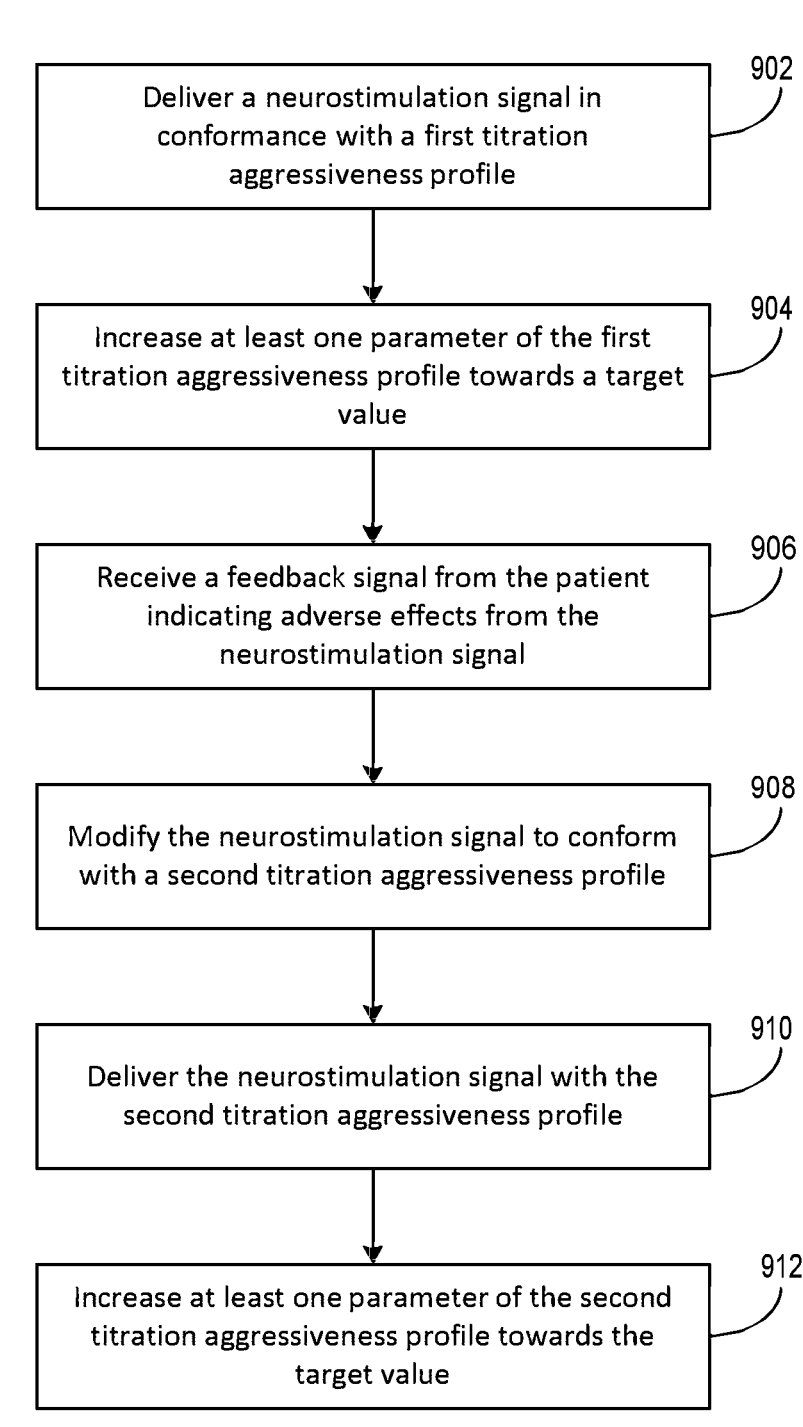

900

902
Deliver a neurostimulation signal in conformance with a first titration aggressiveness profile 904
Increase at least one parameter of the first titration aggressiveness profile towards a target value 906
Receive a feedback signal from the patient indicating adverse effects from the neurostimulation signal 908
Modify the neurostimulation signal to conform with a second titration aggressiveness profile 910
Deliver the neurostimulation signal with the second titration aggressiveness profile 912
Increase at least one parameter of the second titration aggressiveness profile towards the target value

FIG. 9

AUTOMATIC TITRATION WITH DEFIBRILLATION SENSITIVITY COMPENSATION

BACKGROUND

The present disclosure relates generally to neurostimulation and, more specifically, to improved systems and methods for managing titration of stimulation.

Vagus nerve stimulation (VNS) has been used for the clinical treatment of drug-refractory epilepsy and depression, and also as a therapeutic treatment of heart conditions such as chronic heart failure (CHF). VNS therapy commonly requires implantation of a neurostimulator, a surgical procedure requiring several weeks of recovery before the neurostimulator can be activated and a patient can start receiving VNS therapy. Even after the recovery and activation of the neurostimulator, a full therapeutic dose of VNS is not immediately delivered to the patient to avoid causing significant patient discomfort and other undesirable side effects. Instead, to allow the patient to adjust to the VNS therapy, a titration process is utilized in which the intensity is gradually increased over a period of time under a control of a physician, with the patient given time between successive increases in VNS therapy intensity to adapt to the new intensity.

As stimulation is chronically applied at each new intensity level, the patient's tolerance threshold, or tolerance zone boundary, gradually increases, allowing for an increase in intensity during subsequent titration sessions. The titration process can take significantly longer in practice because the increase in intensity is generally performed by a physician or other healthcare provider, and thus, for every step in the titration process to take place, the patient has to visit the provider's office to have the titration adjustments performed. Scheduling conflicts in the provider's office may increase the time between titration sessions, thereby extending the overall titration process, during which the patient in need of VNS does not receive the VNS at the full therapeutic intensity.

As such, providing automated titration of VNS therapy (as well as automated titration of other stimulation-type therapies) is often beneficial for efficiently and effectively providing therapeutic stimulation therapy. However, providing automated titration while accounting for unexpected or unscheduled changes in patient condition presents a variety of challenges that remain unmet by present technologies.

SUMMARY

One embodiment relates to a method of delivering neurostimulation therapy to a patient from an implantable medical device. The method includes delivering, by the implantable medical device, the neurostimulation therapy to the patient. The method further includes determining, by the implantable medical device, that the patient has received a defibrillation shock from a defibrillation device. The method further includes adjusting, by the implantable medical device, the neurostimulation therapy based on determining that the patient has received the defibrillation shock.

Another embodiment relates to a method of delivering neurostimulation therapy to a patient from an implantable medical device. The method includes delivering, by the implantable medical device, the neurostimulation therapy to the patient. The method further includes receiving, by the implantable medical device, a signal from a sensor of the implantable medical device. The method further includes determining, by the implantable medical device, that the patient has received a defibrillation shock from a defibrillation device based on the signal received from the sensor. The method further includes reducing, by the implantable medical device, an intensity of the neurostimulation therapy based on determining that the patient has received the defibrillation shock.

Another embodiment relates to an implantable medical device. The implantable medical device includes at least one processing circuit including at least one processor and at least one memory, the at least one memory having instructions stored thereon that, when executed by the at least one processor, cause the at least one processor to perform operations. The operations include delivering the neurostimulation therapy to a patient. The operations further include determining that the patient has received a defibrillation shock from a defibrillation device. The operations further includes adjusting the neurostimulation therapy based on determining that the patient has received the defibrillation shock.

BRIEF DESCRIPTION OF THE DRAWINGS

Further features, characteristics, and advantages of the present disclosure will become apparent to a person of ordinary skill in the art from the following detailed description of embodiments of the present disclosure, made with reference to the drawings annexed, in which like reference characters refer to like elements.

FIG. 5 is a flowchart of a method for delivering vagus nerve stimulation therapy, according to an example embodiment.

FIGS. 6A and 6B are flowcharts of a titration process, according to an example embodiment.

FIGS. 7A and 7B are block diagrams of neurostimulation systems, according to an example embodiment.

FIG. 9 is a flowchart of a titration process including different titration aggressiveness profiles, according to an example embodiment.

DETAILED DESCRIPTION

Various aspects of the disclosure will now be described with regard to certain examples and embodiments, which are intended to illustrate but not to limit the disclosure. Nothing in this disclosure is intended to imply that any particular feature or characteristic of the disclosed embodiments is essential. The scope of protection is defined by the claims that follow this description and not by any particular embodiment described herein. Before turning to the figures, which illustrate example embodiments in detail, it should be understood that the application is not limited to the details or methodology set forth in the description or illustrated in the figures. It should also be understood that the terminology is for the purpose of description only and should not be regarded as limiting.

The vagus nerve is a diverse nerve trunk that contains both sympathetic and parasympathetic fibers and both afferent and efferent fibers. These fibers have different diameters and myelination and subsequently have different activation thresholds. This results in a graded response as intensity is increased. Low intensity stimulation results in a progressively greater tachycardia, which then diminishes and is replaced with a progressively greater bradycardia response as intensity is further increased. Peripheral neurostimulation therapies that target the fluctuations of the autonomic nervous system have been shown to improve clinical outcomes in some patients. Specifically, autonomic regulation therapy results in simultaneous creation and propagation of efferent and afferent action potentials within nerve fibers comprising the cervical vagus nerve. The therapy directly improves autonomic balance by engaging both medullary and cardiovascular reflex control components of the autonomic nervous system. Upon stimulation of the cervical vagus nerve, action potentials propagate away from the stimulation site in two directions, efferently toward the heart and afferently toward the brain. Efferent action potentials influence the intrinsic cardiac nervous system and the heart and other organ systems, while afferent action potentials influence central elements of the nervous system.

In some instances, after receiving a cardiac defibrillation shock, patients experience increased sensitivity to vagus nerve stimulation (VNS). For example, in some instances, these patients report post-defibrillation pain and sensation from VNS at a stimulation intensities that were previously well tolerated. As described herein, an implantable VNS system may either be informed of or detect the application of defibrillation energy to a patient and to automatically adjust stimulation provided to the patient to compensate for this post-defibrillation-shock sensitivity.

Figures 1, 2A, 2B:
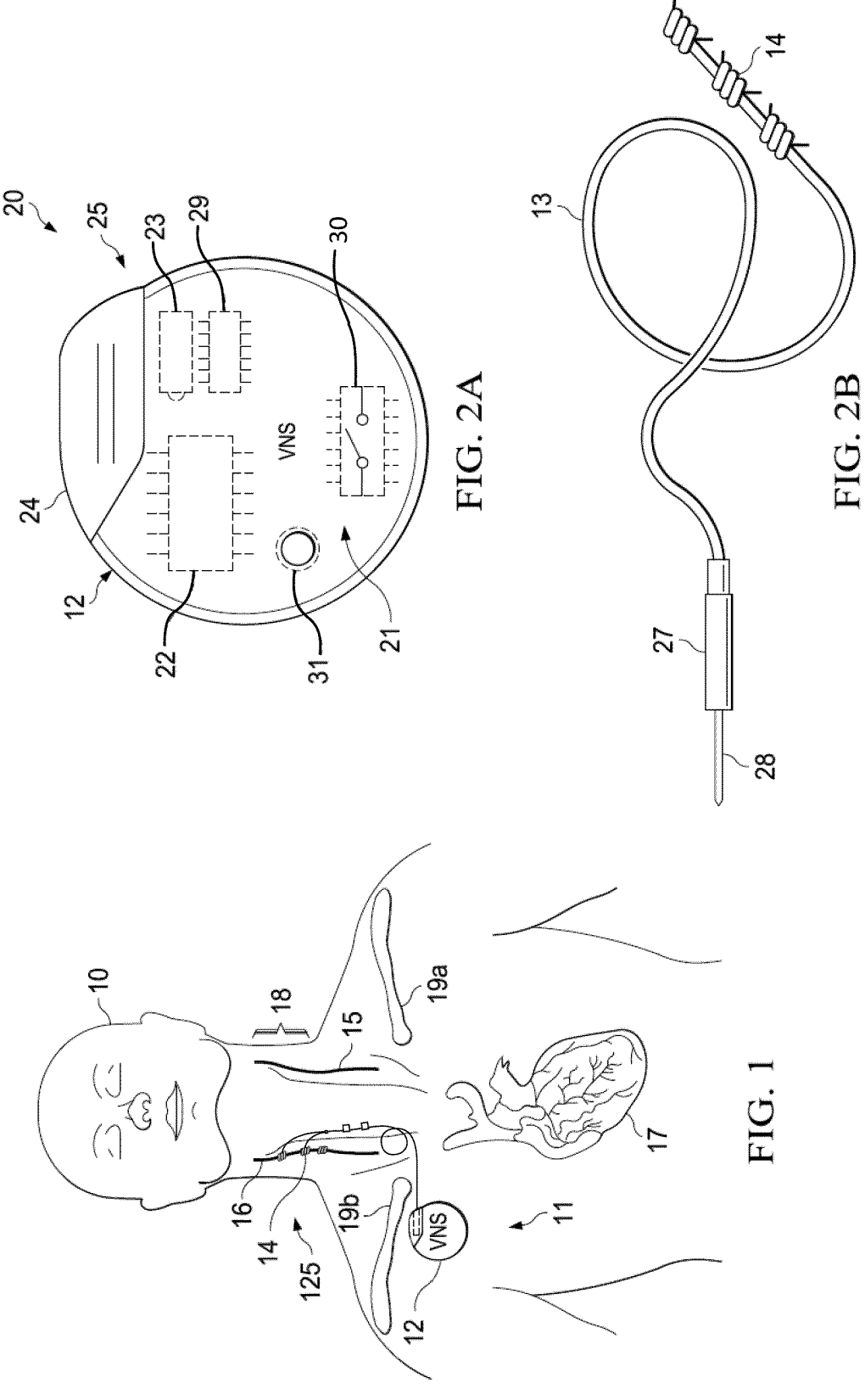
FIG. 1 is a front anatomical diagram showing, by way of example, placement of an implantable vagus stimulation device in a male patient, in accordance with one embodiment.
FIGS. 2A and 2B are diagrams respectively showing the implantable neurostimulator and the stimulation therapy lead of FIG. 1, according to an example embodiment.

For example, in some instances, an implantable vagus nerve stimulator, such as used to treat drug-refractory epilepsy and depression, can be adapted for use in managing chronic cardiac dysfunction (CCD) through therapeutic bi-directional vagus nerve stimulation. FIG. 1 is a front anatomical diagram showing, by way of example, placement of an implantable medical device (e.g., a vagus nerve stimulation (VNS) system 11, as shown in FIG. 1) in a male patient 10, according to an example embodiment. The VNS provided through the stimulation system 11 operates under several mechanisms of action. These mechanisms include increasing parasympathetic outflow and inhibiting sympathetic effects by inhibiting norepinephrine release and adrenergic receptor activation. More importantly, VNS triggers the release of the endogenous neurotransmitter acetylcholine and other peptidergic substances into the synaptic cleft, which has several beneficial anti-arrhythmic, anti-apoptotic, and anti-inflammatory effects as well as beneficial effects at the level of the central nervous system.

The implantable vagus stimulation system 11 comprises an implantable neurostimulator or pulse generator 12 and a stimulating nerve electrode assembly 125. The neurostimulator or pulse generator may be a voltage stimulator or, more preferably, a current stimulator. The stimulating nerve electrode assembly 125, comprising at least an electrode pair, is conductively connected to the distal end of an insulated, electrically conductive lead assembly 13 and electrodes 14. The electrodes 14 may be provided in a variety of forms, such as, e.g., helical electrodes, probe electrodes, cuff electrodes, as well as other types of electrodes.

Figure 3:
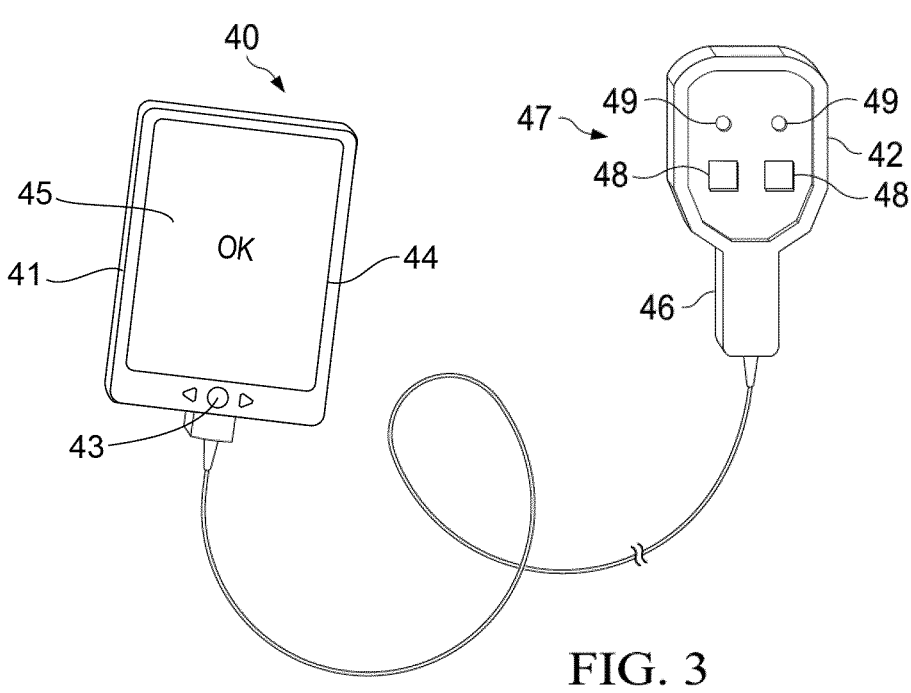
FIG. 3 is a diagram showing an external programmer for use with the implantable neurostimulator of FIG. 1, according to an example embodiment.

The implantable vagus stimulation system 11 can be remotely accessed following implant through an external programmer, such as the programmer 40 shown in FIG. 3 and described in further detail below. The programmer 40 can be used by healthcare professionals to check and program the neurostimulator 12 after implantation in the patient 10 and to adjust stimulation parameters during the stimulation titration process. In some embodiments, an external magnet may provide basic controls. For example, an electromagnetic controller may enable the patient 10 or healthcare professional to interact with the implanted neurostimulator 12 to exercise increased control over therapy delivery and suspension. For further example, an external programmer may communicate with the neurostimulation system 11 via other wired or wireless communication methods, such as, e.g., wireless RF transmission. Together, the implantable vagus stimulation system 11 and one or more of the external components form a VNS therapeutic delivery system.

Figure 4:
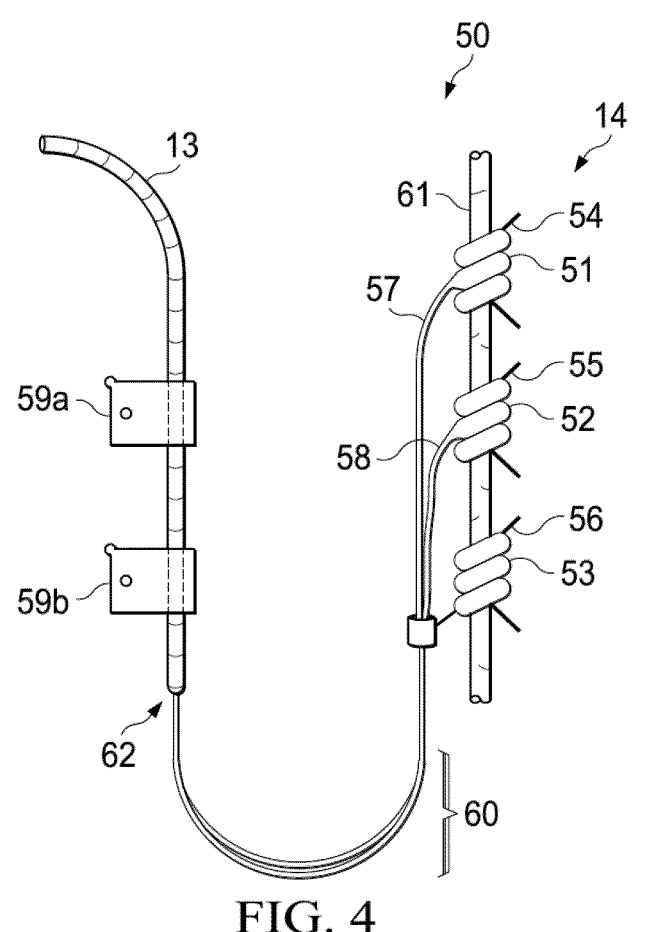
FIG. 4 is a diagram showing electrodes provided as on the stimulation therapy lead of FIG. 2 in place on a vagus nerve in situ, according to an example embodiment.

The neurostimulator 12 is typically implanted in the patient's right or left pectoral region generally on the same side (ipsilateral) as the vagus nerve 15, 16 to be stimulated, although other neurostimulator-vagus nerve configurations, including contra-lateral and bi-lateral are possible. A vagus nerve typically comprises two branches that extend from the brain stem respectively down the left side and right side of the patient, as seen in FIG. 1. The electrodes 14 are generally implanted on the vagus nerve 15, 16 about halfway between the clavicle 19a-b and the mastoid process. The electrodes may be implanted on either the left or right side. The lead assembly 13 and electrodes 14 are implanted by first exposing the carotid sheath and chosen branch of the vagus nerve 15, 16 through a latero-cervical incision (perpendicular to the long axis of the spine) on the ipsilateral side of the patient's neck 18. The helical electrodes 14 are then placed onto the exposed nerve sheath and tethered. A subcutaneous tunnel is formed between the respective implantation sites of the neurostimulator 12 and helical electrodes 14, through which the lead assembly 13 is guided to the neurostimulator 12 and securely connected. Additionally, in various embodiments, the neurostimulator 12 connects to the electrodes 14 as shown in FIG. 4 (e.g., at the top helices).

In one embodiment, the neural stimulation is provided as a low level maintenance dose independent of cardiac cycle. The stimulation system 11 bi-directionally stimulates either the left vagus nerve 15 or the right vagus nerve 16. However, it is contemplated that multiple electrodes 14 and multiple leads 13 could be utilized to stimulate simultaneously, alternatively, or in other various combinations. Stimulation may be through multimodal application of continuously-cycling, intermittent and periodic electrical stimuli, which are parametrically defined through stored stimulation parameters and timing cycles. Both sympathetic and parasympathetic nerve fibers in the vagosympathetic complex are stimulated. Generally, cervical vagus nerve stimulation results in propagation of action potentials from the site of stimulation in a bi-directional manner. The application of bi-directional propagation in both afferent and efferent directions of action potentials within neuronal fibers comprising the cervical vagus nerve improves cardiac autonomic balance. Afferent action potentials propagate toward the parasympathetic nervous system's origin in the medulla in the nucleus ambiguus, nucleus tractus solitarius, and the dorsal motor nucleus, as well as towards the sympathetic nervous system's origin in the intermediolateral cell column of the spinal cord. Efferent action potentials propagate toward the heart 17 to activate the components of the heart's intrinsic nervous system. Either the left or right vagus nerve 15, 16 can be stimulated by the stimulation system 11. The right vagus nerve 16 has a moderately lower (approximately 30%) stimulation threshold than the left vagus nerve 15 for heart rate effects at the same stimulation frequency and pulse width.

The VNS therapy is delivered autonomously to the patient's vagus nerve 15, 16 through three implanted components that include a neurostimulator 12, lead assembly 13, and electrodes 14. FIGS. 2A and 2B are diagrams respectively showing the implantable neurostimulator 12 and the stimulation lead assembly 13 of FIG. 1. The stimulation lead assembly 13 and electrodes 14 are generally fabricated as a combined assembly although other types of single-pin receptacle-compatible therapy leads and electrodes could also be used.

Referring first to FIG. 2A, the system 20 may be configured to provide multimodal vagus nerve stimulation. In a maintenance mode, the neurostimulator 12 is parametrically programmed to deliver continuously-cycling, intermittent and periodic ON-OFF cycles of VNS. Such delivery produces action potentials in the underlying nerves that propagate bi-directionally, both afferently and efferently.

In some instances, the neurostimulator 12 includes an electrical pulse generator that is tuned to improve autonomic regulatory function by triggering action potentials that propagate both afferently and efferently within the vagus nerve 15, 16. The neurostimulator 12 is enclosed in a hermetically sealed housing 21 constructed of a biocompatible material, such as titanium. The housing 21 contains electronic circuitry 22 powered by a battery 23, such as a lithium carbon monofluoride primary battery or a rechargeable secondary cell battery. The electronic circuitry 22 may be implemented using complementary metal oxide semiconductor integrated circuits that include a microprocessor controller that executes a control program according to stored stimulation parameters and timing cycles; a voltage regulator that regulates system power; logic and control circuitry, including a recordable memory 29 within which the stimulation parameters are stored, that controls overall pulse generator function, receives and implements programming commands from the external programmer, or other external source, collects and stores telemetry information, processes sensory input, and controls scheduled and sensory-based therapy outputs; a transceiver that remotely communicates with the external programmer using radio frequency signals; an antenna, which receives programming instructions and transmits the telemetry information to the external programmer; and a reed switch 30 that provides remote access to the operation of the neurostimulator 12 using an external programmer, a simple patient magnet, or an electromagnetic controller. The recordable memory 29 can include both volatile (dynamic) and non-volatile/persistent (static) forms of memory, within which the stimulation parameters and timing cycles can be stored. Other electronic circuitry and components are possible.

The neurostimulator 12 includes a header 24 to securely receive and connect to the lead assembly 13. In one embodiment, the header 24 encloses a receptacle 25 into which a single pin for the lead assembly 13 can be received, although two or more receptacles could also be provided, along with the corresponding electronic circuitry 22. The header 24 may internally include a lead connector block (not shown), a setscrew, and a spring contact (not shown) that electrically connects to the lead ring, thus completing an electrical circuit.

In some embodiments, the housing 21 may also contain a physiological sensor 31 that is electrically interfaced with the logic and control circuitry. In some instances, the physiological sensor 31 may receive, for example, the patient's sensed heart rate as a sensory input. In these instances, the physiological sensor 31 may monitor the patient's heart rate using an ECG-type electrode. Through the electrode, the patient's heartbeat can be sensed by detecting ventricular depolarization. In a further embodiment, a plurality of electrodes can be used to sense voltage differentials between electrode pairs, which can undergo signal processing for cardiac physiological measures, for instance, detection of the P-wave, QRS complex, and T-wave. Accordingly, in some embodiments, the physiological sensor 31 may provide the sensed heart rate to the control and logic circuitry as a sensory input that can be used to determine the onset or presence of arrhythmias, particularly VT, and/or to monitor and record changes in the patient's heart rate over time or in response to applied stimulation signals.

In some other embodiments, the physiological sensor 31 may instead be configured to receive or detect, for example, ECG signals, internal voltage measurements, or acceleration within the patient. For example, as will be described further below, in some instances, the physiological sensor 31 may be configured to detect or receive the ECG signals, internal voltage measurements, or acceleration within the patient to aid in the detection of an internal or external defibrillation shock received by the patient. This detection of the internal or external defibrillation shock received by the patient may allow for the neurostimulator 12 to automatically adjust a stimulation titration scheme provided to the patient to account for a post-defibrillation-shock heightened level of stimulation sensitivity, as will be further discussed below. It should be appreciated that, in some instances, the neurostimulator 12 may include a plurality of physiological sensors similar to the physiological sensor 31, such that the neurostimulator may be configured to receive and/or detect a plurality of the aforementioned physiological measurements.

Referring next to FIG. 2B, the lead assembly 13 delivers an electrical signal from the neurostimulator 12 to the vagus nerve 15, 16 via the electrodes 14. On a proximal end, the lead assembly 13 has a lead connector 27 that transitions an insulated electrical lead body to a metal connector pin 28 with a metal connector ring. During implantation, the connector pin 28 is guided through the receptacle 25 into the header 24 and securely fastened in place using the setscrew (not shown) to electrically couple one electrode of the lead assembly 13 to the neurostimulator 12 while a spring contact (not shown) makes electrical contact to the ring connected to the other electrode. On a distal end, the lead assembly 13 terminates with the electrode 14, which bifurcates into a pair of anodic and cathodic electrodes 62 (as further described infra with reference to FIG. 4). In one embodiment, the lead connector 27 is manufactured using silicone, and the connector pin 28 and ring are made of stainless steel, although other suitable materials could be used, as well. The insulated lead body of the lead assembly 13 utilizes a silicone-insulated alloy conductor material.

In some embodiments, the electrodes 14 are helical and placed around the cervical vagus nerve 15, 16 at the location below where the superior and inferior cardiac branches separate from the cervical vagus nerve. In alternative embodiments, the helical electrodes may be placed at a location above where one or both of the superior and inferior cardiac branches separate from the cervical vagus nerve. In one embodiment, the helical electrodes 14 are positioned around the patient's vagus nerve oriented with the end of the helical electrodes 14 facing the patient's head. In an alternate embodiment, the helical electrodes 14 are positioned around the patient's vagus nerve 15, 16 oriented with the end of the helical electrodes 14 facing the patient's heart 17. At the distal end, the insulated electrical lead body of the lead assembly 13 is bifurcated into a pair of lead bodies that are connected to a pair of electrodes. The polarity of the electrodes could be configured into a proximal anode and a distal cathode, or a proximal cathode and a distal anode.

The neurostimulator 12 may be interrogated prior to implantation and throughout the therapeutic period with a healthcare provider-operable control system comprising, for example, an external programmer and programming wand (shown in FIG. 3) for checking proper operation, downloading recorded data, diagnosing problems, and programming operational parameters. FIG. 3 is a diagram showing an external programmer 40 for use with the implantable neurostimulator 12 of FIG. 1. The external programmer 40 includes a healthcare provider operable programming computer 41 and a programming wand 42. Generally, use of the external programmer is restricted to healthcare providers, while more limited manual control is provided to the patient through "magnet mode."

In one embodiment, the external programmer 40 executes application software 45 specifically designed to interrogate the neurostimulator 12. The programming computer 41 interfaces to the programming wand 42 through a wired or wireless data connection. Other configurations and combinations of external programmer 40, programming wand 42, and application software 45 are possible.

The programming computer 41 can be implemented using a general purpose programmable computer and can be a personal computer, laptop computer, ultrabook computer, netbook computer, handheld computer, tablet computer, smart phone, or other form of computational device. For example, in one embodiment, the programming computer 41 is a tablet programmer with a wired or wireless data connection to the programming wand 42. The programming computer 41 functions through those components conventionally found in such devices, including, for instance, a central processing unit, volatile and persistent memory, touch-sensitive display, control buttons, peripheral input and output ports, and network interface. The computer 41 operates under the control of the application software 45, which is executed as program code as a series of process or method modules or steps by the programmed computer hardware. Other assemblages or configurations of computer hardware, firmware, and software are possible.

Operationally, the programming computer 41, when connected to a neurostimulator 12 through wireless telemetry using the programming wand 42, can be used by a healthcare provider to remotely interrogate the neurostimulator 12 and modify stored stimulation parameters. The programming wand 42 provides data conversion between the digital data accepted by and output from the programming computer and the radio frequency signal format that is required for communication with the neurostimulator 12. In other embodiments, the programming computer may communicate with the implanted neurostimulator 12 using other wireless communication methods, such as wireless RF transmission. The programming computer 41 may further be configured to receive inputs, such as physiological signals received from patient sensors (e.g., implanted or external). These sensors may be configured to monitor one or more physiological signals, e.g., vital signs, such as body temperature, pulse rate, respiration rate, blood pressure, etc. These sensors may be coupled directly to the programming computer 41 or may be coupled to another instrument or computing device which receives the sensor input and transmits the input to the programming computer 41. The programming computer 41 may monitor, record, and/or respond to the physiological signals in order to effectuate stimulation delivery in accordance with some embodiments.

The healthcare provider operates the programming computer 41 through a user interface that includes a set of input controls 43 (e.g., including a touchscreen of the programming computer 41) and a visual display 44, which could be touch-sensitive, upon which to monitor progress, view downloaded telemetry and recorded physiology, and review and modify programmable stimulation parameters. The telemetry can include reports on device history that provide patient identifier, implant date, model number, serial number, magnet activations, total ON time, total operating time, manufacturing date, and device settings and stimulation statistics, and on device diagnostics that include patient identifier, model identifier, serial number, firmware build number, implant date, communication status, output current status, measured current delivered, lead impedance, and battery status. Other kinds of telemetry or telemetry reports are possible.

During interrogation, the programming wand 42 is held by its handle 46 and the bottom surface 47 of the programming wand 42 is placed on the patient's chest over the location of the implanted neurostimulator 12. A set of indicator lights 49 can assist with proper positioning of the wand and a set of input controls 48 enable the programming wand 42 to be operated directly, rather than requiring the healthcare provider to awkwardly coordinate physical wand manipulation with control inputs via the programming computer 41. The sending of programming instructions and receipt of telemetry information occur wirelessly through radio frequency signal interfacing. Other programming computer and programming wand operations are possible.

FIG. 4 is a diagram showing the helical electrodes 14 provided as on the stimulation lead assembly 13 of FIG. 2 in place on a vagus nerve 15, 16 in situ 50. Although described with reference to a specific manner and orientation of implantation, the specific surgical approach and implantation site selection particulars may vary, depending upon physician discretion and patient physical structure.

Under one embodiment, helical electrodes 14 may be positioned on the patient's vagus nerve 61 oriented with the end of the helical electrodes 14 facing the patient's head. At the distal end, the insulated electrical lead body of the lead assembly 13 is bifurcated into a pair of lead bodies 57, 58 that are connected to a pair of electrodes 51, 52. The polarity of the electrodes 51, 52 could be configured into a proximal anode and a distal cathode, or a proximal cathode and a distal anode. In addition, an anchor tether 53 is fastened over or in connection with the lead bodies 57, 58 that maintains the helical electrodes' position on the vagus nerve 61 following implant. In one embodiment, the conductors of the electrodes 51, 52 are manufactured using a platinum and iridium alloy, while the helical materials of the electrodes 51, 52 and the anchor tether 53 are a silicone elastomer.

During surgery, the electrodes 51, 52 and the anchor tether 53 are coiled around the vagus nerve 61 proximal to the patient's head, each with the assistance of a pair of sutures 54, 55, 56, made of polyester or other suitable material, which help the surgeon to spread apart the respective helices. The lead bodies 57, 58 of the electrodes 51, 52 are oriented distal to the patient's head and aligned parallel to each other and to the vagus nerve 61. A strain relief bend 60 can be formed on the distal end with the insulated electrical lead body of the lead assembly 13 aligned, for example, parallel to the helical electrodes 14 and attached to the adjacent fascia by a plurality of tie-downs 59*a-b*.

The neurostimulator 12 delivers VNS under control of the electronic circuitry 22. The stored stimulation parameters are programmable. Each stimulation parameter can be independently programmed to define the characteristics of the cycles of therapeutic stimulation and inhibition to ensure optimal stimulation for a patient 10. The programmable stimulation parameters include output current, signal frequency, pulse width, signal ON time, signal OFF time, magnet activation (for VNS specifically triggered by "magnet mode"), post-defibrillation-shock response parameters, and reset parameters. Other programmable parameters are possible. In addition, sets or "profiles" of preselected stimulation parameters can be provided to physicians with the external programmer and fine-tuned to a patient's physiological requirements prior to being programmed into the neurostimulator 12.

Therapeutically, the VNS may be delivered as a multi-modal set of therapeutic doses, which are system output behaviors that are pre-specified within the neurostimulator 12 through the stored stimulation parameters and timing cycles implemented in firmware and executed by the microprocessor controller. The therapeutic doses include a maintenance dose that includes continuously-cycling, intermittent and periodic cycles of electrical stimulation during periods in which the pulse amplitude is greater than 0 mA ("therapy ON") and during periods in which the pulse amplitude is 0 mA ("therapy OFF").

The neurostimulator 12 can operate either with or without an integrated heart rate sensor. Additionally, where an integrated leadless heart rate monitor is available, the neurostimulator 12 can provide autonomic cardiovascular drive evaluation and self-controlled titration. The neurostimulator 12 can additionally be used to counter natural circadian sympathetic surge upon awakening and manage the risk of cardiac arrhythmias during or attendant to sleep, particularly sleep apneic episodes. In some instances, the neurostimulator 12 can automatically alter stimulation and/or stimulation titration parameters in response to detected defibrillation shocks applied to the patient (e.g., from external or implanted defibrillation devices).

Several classes of implantable medical devices provide therapy using electrical current as a stimulation vehicle. When such a system stimulates certain organs or body structures like the vagus nerve, therapeutic levels of electrical stimulation are usually not well tolerated by patients without undergoing a process known as titration. Titration is a systematic method or process of incrementally increasing the stimulation parameters employed by an implanted device to deliver a stimulation current to the patient at increasing levels that achieve or improve therapeutic benefit while minimizing side effects that could disrupt the stimulation therapy. Titration in a neuromodulation system may be necessary due to centrally-mediated side effects elicited by large changes in stimulation intensity. For example, the neuromodulation system may be unable to instantly change the intensity of delivered neurostimulation from an inactive state (e.g., stimulation programmed to OFF) to full therapeutic intensity without the patient experiencing adverse effects (e.g., triggering an expiratory cough reflex). That being said, the central processing areas of vagal afferents recruited at low stimulation intensity can often handle small stimulation intensity increases over periods of time without effect.

As such, titration usually involves bringing the patient to an initial stimulation level that is tolerable to the patient (i.e., below an initial tolerance threshold), waiting for a period of time for the patient to adjust to the continuing delivery of the initial stimulation level and to define a higher tolerance threshold of the patient, and then increasing the initial stimulation level to a higher stimulation level that is, in some patients, greater than the initial tolerance threshold, and so on. This process is repeated in sequences that progress from a stimulation delivery provided over a waiting period, and then to an increase in a stimulation level that defines the next sequence of the stimulation delivery and the next waiting period. The central neural processors gradually remodel and accommodate the increasing stimulation intensity if given sufficient time between increasing stimulation steps (e.g., function without adverse effects such as triggering the cough reflex).

FIG. 5 is a flow diagram showing a method for delivering vagus nerve stimulation therapy, according to an example embodiment. A titration process 400 is used to gradually increase the stimulation intensity to a desired therapeutic level or maintenance dosage level. If the stimulation intensity is increased too quickly before the patient is fully accommodated to the stimulation signal, the patient may experience undesirable side effects, such as coughing, hoarseness, throat irritation, or expiratory reflex. The titration process gradually increases stimulation intensity within a tolerable level and maintains that intensity for a period of time to permit the patient to adjust to each increase in intensity, thereby gradually increasing the patient's side effect tolerance zone boundary to so as to accommodate subsequent increases in intensity. The titration process continues until adequate adaptation is achieved. In embodiments, the titration process is automated and is executed by the implanted device without manual adjustment of the stimulation intensity by the subject or health care provider. As will be described in greater detail below, in some instances, adequate adaptation may be a composite threshold comprising one or more of the following: an acceptable side effect level, a target intensity level, and a target physiological response. In some embodiments, adequate adaption includes all three objectives: an acceptable side effect level, a target intensity level, and a target physiological response.

In some embodiments, the titration process is a mix of automation and physician input. In some instances, a physician may use intermediate holds to stop the automated titration at certain thresholds (e.g., a certain number of days or weeks, certain stimulation parameter values, etc.) and evaluate the patient before resuming the automated titration. The physician may receive a graphical titration history to review how the automated titration process has been progressing from one sequence to the next. The graphical titration history may include markers. The markers may represent intermediate holds, when target parameters are reached between adjacent sequences, etc. After the physician has resumed the automatic titration, the next sequence of automated titration may progress until the next intermediate hold is reached.

As described above, it may be desirable to minimize the amount of time required to complete the titration process so as to begin delivery of the stimulation at therapeutically desirable levels, particularly when the patient is being treated for an urgent condition such as CHF. In addition, it is desirable to utilize a maintenance dose intensity at the minimum level required to achieve the desired therapeutic effect. This can reduce power requirements for the neurostimulator and reduce patient discomfort.

It has been observed that a patient's side effect profile is more sensitive to the stimulation output current than to the other stimulation parameters, such as frequency, pulse width, and duty cycle. As a result, accommodation to the stimulation output current is a primary factor in completing the titration process. It has also been observed that if the other stimulation parameters are maintained at a level below the target levels, the output current can be increased to higher levels without eliciting undesirable side effects that would be result when the other parameters are at the target level. As a result, increasing the target output current while maintaining the other stimulation parameters (pulse width in particular) at reduced levels can result in a faster accommodation and shorter overall titration time than would be achieved by attempting to increase the output current while stimulating at the target pulse width.

Referring again to FIG. 5, in step 401, a stimulation system 11, including a neurostimulator 12, a nerve stimulation lead assembly 13, and a pair of electrodes 14, is implanted in the patient. In step 402, the patient undergoes an optional post-surgery recovery period, during which time the surgical incisions are allowed to heal and no VNS therapy occurs. This period may last, e.g., two weeks post-surgery. In step 403, the stimulation therapy is initiated with the initiation of a titration process. During this titration process, VNS therapy is titrated by adjusting one or more of the stimulation parameters, including output current, pulse width, signal frequency, and duty cycle, as will be described in greater detail below. Completion of the titration process determines the stimulation intensity to be used for subsequent maintenance doses delivered in step 404. These maintenance doses may be selected to provide the minimum stimulation intensity necessary to provide the desired therapeutic result.

FIG. 6A is a flow diagram illustrating a titration process 500, according to an example embodiment. Process 500 includes setting titration parameters (step 501), initiating titration (step 502), stopping titration at an intermediate hold (step 503), and resuming titration (step 504).

In step 501, a physician sets the titration parameters via programmer 40, which are received by the implantable vagus nerve stimulation system 11. In some embodiments, the titration parameters may be defined by one or more titration algorithms that may be selected by the physician, or may be presented to the physician as a preferred or recommended list of titration parameters that the programming physician can adopt. In other embodiments, rather than present the physician with a set titration algorithm with fixed algorithm values, the physician may be presented with default values that could be manually adjusted. The titration parameter starting values, target values, and/or increment values for amplitude, pulse width, frequency, and/or duty cycle may be adjustable, as may the time interval between titration steps. Time of day and delay to therapy start may also be programmable as a titration parameter. The titration parameters may also include one or more intermediate holds that maintain certain parameters until the physician indicates that the automated titration can continue. The physician may be limited so that modification can be made to only a select group of parameters, or some parameters may be considered to be in a locked state until unlocked by the physician. In some embodiments, the physician is able to modify a large number of titration parameters (e.g., 10-12 parameters).

Alternatively, rather than give the physician control over the titration parameter values themselves, the physician's options for the titration process may be presented as a set of "aggressiveness" options to select from, each of which would be used by the system to determine the values to use. For example, the physician may be able to choose from an aggressive profile, a moderate profile, or a light profile (sensitive) that is appropriate for certain types of patients that do not require detailed titration parameter programming. More or fewer aggressiveness profiles could be used, and the aggressiveness profiles may correspond to the overall health status of the patient, the patient's sensitivity to stimulation therapies or titration processes, the patient's post-defibrillation-shock stimulation sensitivity, and/or the patient's medical history. The aggressiveness profile selected by the physician may result in a predetermined set of titration parameters being selected. The predetermined titration parameters may vary between different aggressiveness profiles, and some titration parameters may remain constant, or similar, between various aggressiveness profiles. For example, the aggressive profile may be suitable for patients that have a high toleration for the titration process and may include shorter time intervals between titration steps, higher intensity target values, and/or larger increment values (e.g., as compared to the moderate or light profiles) that may result in an achievement of a suitable therapy level more quickly as compared to the moderate or light profiles. While some of the parameters may promote a more aggressive titration progression, some of the parameters may be consistent with parameters of other profiles (e.g., titration holds).

In some embodiments, each of the aggressiveness profiles may be mapped by the system to a set of parameters or a range of parameters. For example, if the user selects the aggressive profile, the system may receive the user selection and set the values of one or more parameters (e.g., amplitude, pulse width, frequency, duty cycle, intervals between titration steps, and/or other parameters) to a first set of values. If the user selects the moderate profile, the system may set the values of the parameters to a second predetermined set or range of values that is different than the set associated with the aggressive profile. In some embodiments, the physicians are limited to modification of the parameters within a range of boundary values. The ranges may be for the default parameters, or may be set individually for the aggressiveness options (e.g., the ranges for the aggressive profile and the moderate profile may be different, but may overlap for some parameters). The physician may be able to customize the parameters in the preset profiles. Titrating according to aggressiveness profiles is described in further detail below with respect to FIGS. 8 and 9. In step 502, the physician initiates titration using the titration parameters defined at 501.

In step 503, titration is stopped at a titration hold. The titration hold may be an intermediate hold set by the physician during step 501. The VNS system 11 may perform automated titration according to process 600, described below. However, the physician is given the option (through the programmer 40) to designate intermediate points at which the titration algorithm would pause and await manual (programmer-based) activation by the physician. These hold points may be either time based (e.g. after 2, 4, 6, and/or 8 weeks of titration) or stimulation based (e.g. once stimulation amplitude reaches 1.0, 1.5, 2.0, and/or 2.5 mA). This would allow the physician to evaluate the patient in the clinic before deciding to continue titration. The physician releases the hold on the titration with the programmer 40 once the patient has been evaluated. The physician may also modify parameters during the clinical evaluations.

The holds may be predefined for the entire titration process during initial set up. Alternatively, the physician may have the option of setting a new intermediate hold when evaluating the patient. The intermediate holds may be consistent throughout the titration process (e.g., every 2 weeks, every 0.5 mA, etc.). In another embodiment, the intermediate holds are different for at least one hold (e.g., 4 weeks to the first hold, 2 weeks for every subsequent hold, etc.). In another embodiment, intermediate holds can be a combination of parameters (e.g., amplitude and pulse width). In some embodiments, the hold may be set to begin when both parameters are met or when one parameter is met. In another embodiment, one parameter cannot exceed the hold value and will remain constant until the second parameter is reached. In some embodiments, both parameters will progress according to the automated titration until both parameters meet the intermediate hold value, but one parameter may exceed the intermediate hold until the second parameter reaches the intermediate hold value. The physician may have the option to set as many or as few intermediate holds as desired.

During the automated titration between intermediate holds, the VNS system 11 may be fully automated or partially automated. In some embodiments, titration is performed without any intervention from either the patient or the healthcare provider. This embodiment also automatically detects patient side effects and intolerance and adjusts stimulation parameters to remain below the side effect threshold, as is described with respect to FIG. 6B. In another embodiment, the VNS system 11 may automatically adjust stimulation parameters slowly over time, without any additional intervention from the healthcare provider. Because the system may not be able to determine if stimulation causes an intolerable side effect, it may be configured to rely on the patient to swipe a magnet to indicate an intolerable level of a side effect. The VNS system 11 may then adjust stimulation parameters in response to patient magnet activation.

For example, patients may require a total of 10±2 clinic visits over a 10-week period to reach the target stimulation intensity. The frequency of required clinic visits is bothersome to both patients and providers and creates a barrier to therapy adoption. In addition, the frequency of required clinic visits extends the time required to titrate patients to the target stimulation intensity. However, the physician may be skeptical of completely automated titration and want to ensure the patients are not experiencing intolerable side effects and are adapting to stimulation adequately. By allowing the physician to set the parameters, and evaluate the patient intermediately, but still allow titration to perform automatically between visits, the time period to reach the target stimulation may be reduced, while giving the physicians more control over the titration process. Preferably, the number of clinic visits needed and the overall timeframe of the titration process is reduced by only the use of intermediate holds. Any time penalty related to the intermediate holds is believed to be significantly less than the time penalty resulting from an automated titration process that causes side effect and ultimately requires the patient to undergo a re-titration protocol.

In step 504, titration is resumed. The physician may resume titration using the programmer 40 after evaluation of the patient. When the physician resumes titration, he or she may have the option to modify stimulation parameters and/or intermediate holds. The titration may resume using automated titration until the next intermediate hold is reached. This process may continue until the therapy parameters are reached.

Figure 6B:
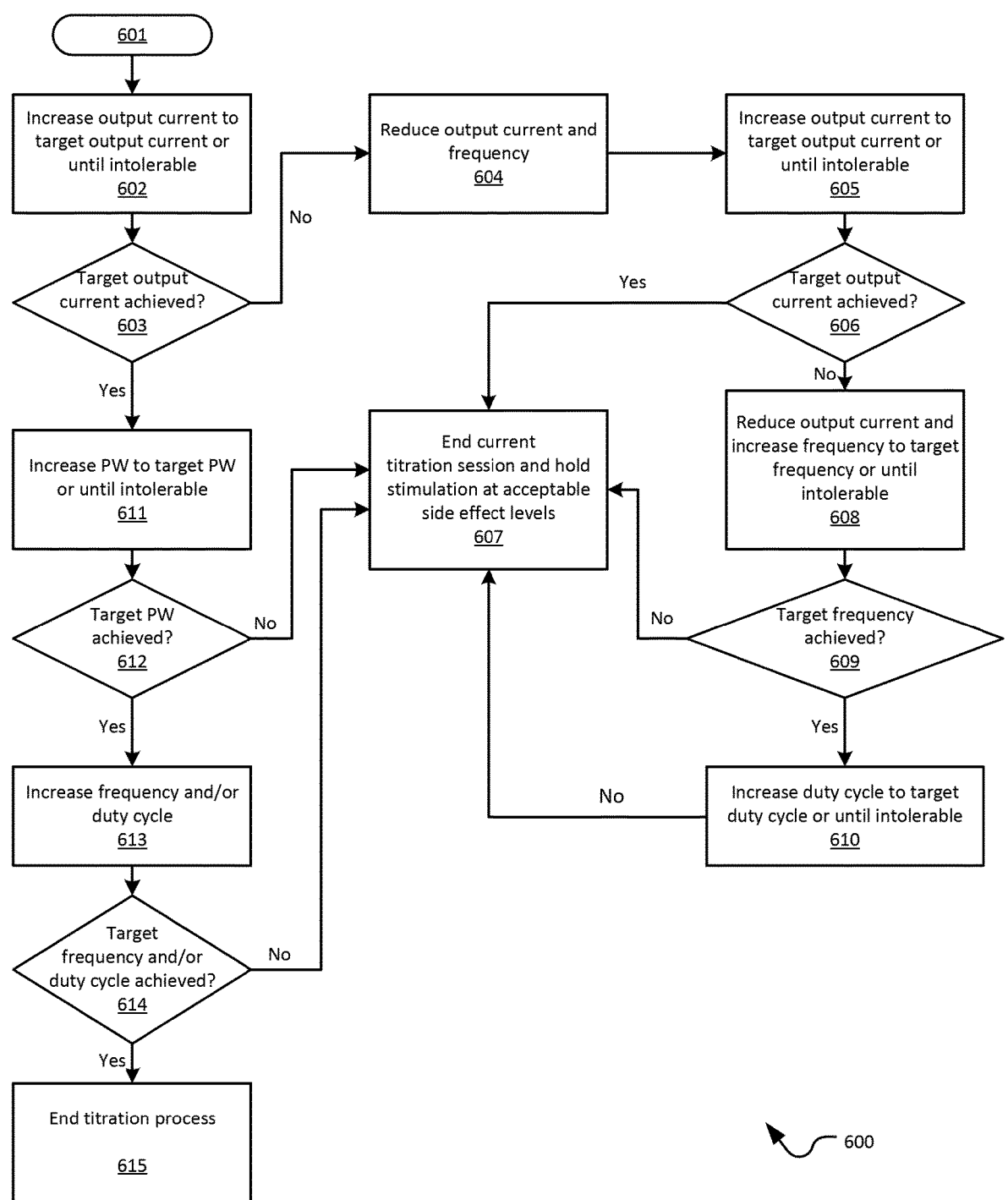

FIG. 6B is a flow diagram illustrating a titration process 600 in accordance with and example embodiment. When first initiating the titration process, the neurostimulator 12 is configured to generate a stimulation signal having an initial stimulation parameter set. The initial parameter set may comprise an initial output current, an initial frequency, an initial pulse width, and an initial duty cycle. The various initial parameter settings may vary but may be selected so that one or more of the parameters are set at levels below a predefined target parameter set level, such that the titration process is used to gradually increase the intensity parameters to achieve adequate adaptation. In some embodiments, the initial frequency is set at the target frequency level, while the initial output current, initial pulse width, and initial duty cycle are set below their respective target levels. In one embodiment, the target parameter set comprises a 5 Hz frequency, 250 μsec pulse width, a duty cycle of 14 sec ON and 66 seconds OFF, and an output current of between 1.5 mA-3.0 mA (e.g., 2.5 mA for right side stimulation and 3.0 mA for left side stimulation), and the initial parameter set comprises 5 Hz frequency, 130 μsec pulse width, a duty cycle of 14 sec ON and 66 seconds OFF, and an output current of between 0.25 mA-0.5 mA. In other embodiments, the target parameter set includes a 10 Hz frequency that is used instead of a 5 Hz frequency. The initial parameter set may also include one or more intermediate holds as discussed with respect to FIG. 6A. However, this is an example embodiment and these values are not intended to be limiting. Other frequencies, pulse widths, duty cycles and output currents may be implemented. The initial and target parameters may vary from patient to patient based on the patient's sensitivity to stimulation. While the initial parameters are shown to be equal to the target parameters for some of the exemplary parameters (e.g., frequency and duty cycle), some or all of the parameters may have initial parameters that differ from the target parameters.

In step 601, the stimulation system delivers stimulation to the patient. If this is the first titration session, then the stimulation would be delivered with the initial stimulation parameter set described above. If this is a subsequent titration session, then the stimulation intensity would remain at the same level provided at the conclusion of the previous titration session. Alternatively, the subsequent titration session can start at a level that is set by the physician, e.g., at the next titration level that follows the level provided at the conclusion of the previous titration session.

In step 602, the output current is gradually increased until the stimulation results in an intolerable side effect level, the target intensity (e.g., 2.5 mA at a pulse width of 250 us and a frequency of 10 Hz) is reached, or adequate adaptation is achieved. As described above, adequate adaptation is a composite threshold comprising one or more of the following: an acceptable side effect level, a target intensity level, and a target physiological response. In accordance with some embodiments, the target physiological response comprises a target heart rate change during stimulation. The patient's heart rate may be monitored using an implanted or external heart rate monitor, and the patient's heart rate during stimulation is compared to the patient's baseline heart rate to determine the extent of heart rate change. In accordance with some embodiments, the target heart rate change is a heart rate change of between 4% and 5%. If at any point during the titration process 600 adequate adaptation is achieved, the titration process ends, and the stimulation intensity which resulted in the adequate adaptation is used for ongoing maintenance dose therapy delivery.

The output current may be increased in any desired increment, but small increments, e.g., 0.1 mA or 0.25 mA, may be desirable so as to enable more precise adjustments. In some cases, the output current increments may be determined by the neurostimulator's maximum control capability. During the initial titration sessions, it is likely that the patient's side effect tolerance zone boundary will be reached well before the output current reaches the target level or adequate adaptation is achieved. At decision step 603, if the target output current has not been achieved but the maximum tolerable side effects have been exceeded, the process proceeds to step 604.

In step 604, the output current is reduced one increment to bring the side effects within acceptable levels. In addition, the frequency is reduced. In embodiments in which the initial frequency was 10 Hz, in step 604, the frequency may be reduced, e.g., to 5 Hz or 2 Hz.

Next, in step 605, the output current is gradually increased again at the reduced frequency level until the stimulation results in an intolerable side effect level or the target output current (e.g., 2.5 mA) is reached. At decision step 606, if the target output current has been reached and the maximum tolerable side effects have not been exceeded, the process proceeds to step 607 where the titration session is concluded. The stimulation system may be programmed to continue delivering the stimulation signal at the last parameter settings achieved prior to conclusion of the titration session. After a period of time, another titration session may be initiated and the process returns to step 601. This can be any period of time sufficient to permit the patient to adjust to the increased stimulation levels. This can be, for example, as little as approximately two or three days, approximately one to two weeks, approximately four to eight weeks, or any other desired period of time.

In some embodiments, the titration sessions are automatically initiated by the stimulation system or initiated by the patient without requiring any intervention by the health care provider. This can eliminate the need for the patient to schedule a subsequent visit to the health care provider, thereby potentially reducing the total amount of time needed for the titration process to complete. In these embodiments, the stimulation system may include a physiological monitor, e.g., an implanted heart rate sensor, that communicates with the stimulation system's control system to enable the control system to detect the patient's physiological response to the titration and automatically make adjustments to the titration processes described herein with reduced or no inputs from the patient or health care provider. The monitored signals can also enable the control system to detect when the target physiological response has been achieved and conclude the titration process. The stimulation system could in addition or alternatively include a patient control input to permit the patient to communicate to the control system that the acceptable side effect level has been exceeded. This control input may comprise an external control magnet that the patient can swipe over the implanted neurostimulator or other internal or external communication device that the patient can use to provide an input to the control system. In these automatically-initiated titration sessions, the stimulation system may be configured to wait a period of time after completing one session before initiating the next session. This period of time may be predetermined, e.g., two or three days, or programmable. In another embodiment, the stimulation system is configured to wait until authorization has been received before initiating the next session (i.e., an intermediate hold).

Returning to decision step 606, if the target output current has not been reached but the maximum tolerable side effects have been exceeded, the process proceeds to step 608. In step 608, the output current is reduced one increment to restore an acceptable side effect condition, and the frequency is gradually increased until the stimulation results in an intolerable side effect level or the target frequency (e.g., 5 Hz) is reached. At decision step 609, if the target frequency has not been reached but the maximum tolerable side effects have been exceeded, the frequency is reduced to restore an acceptable side effect level and the process proceeds to step 607. Again, in step 607, the current titration session is concluded, and the stimulation system may be programmed to continue delivering the stimulation signal at the last parameter settings achieved prior to conclusion of the titration session.

At decision step 609, if the target frequency has been reached before the maximum tolerable side effects have been exceeded, the duty cycle is gradually increased until the stimulation results in an intolerable side effect level or the target duty cycle (e.g., 14 sec ON and 66 sec OFF) is reached, at which point the process proceeds to step 607 and the titration session is concluded and ongoing stimulation delivered at the last intensity eliciting acceptable side effect levels.

Returning to decision step 603, if the target output current has been achieved before the maximum tolerable side effects are exceeded, the process proceeds to step 611. In step 611, the pulse width is gradually increased until the stimulation results in an intolerable side effect level or the target pulse width (e.g., 250 µsec) is reached. In some embodiments, before step 611, the output current is reduced (e.g., by up to 50%), and the pulse width may be increased in step 611 at that reduced output current. After the target pulse width is achieved, the output current may be restored to the target output current. In other embodiments, the output current may be reduced (or may be retained at the reduced level established prior to step 611, as described above), and the frequency and duty cycle are gradually increased in step 613 at that reduced output current. This reduction in output current after achieving the target output current may enable the patient to maintain tolerability with increasing pulse width, frequency, and duty cycle in subsequent titration steps.

At decision step 612, if the target pulse width has not been achieved before the maximum tolerable side effects have been exceeded, the pulse width is reduced to restore an acceptable side effect level and the process proceeds to step 607. Again, in step 607, the current titration session is concluded.

If at decision step 612, the target pulse width has been achieved before the maximum tolerable side effects have been exceeded, the process proceeds to step 613. In step 613, the frequency and/or duty cycle are increased until the stimulation results in an intolerable side effect level or the target frequency and target duty cycle are reached. The frequency and duty cycle can be increased in step 612 simultaneously, sequentially, or on an alternating basis.

At decision step 614, if the target frequency and/or target duty cycle have not been achieved before the maximum tolerable side effects have been exceeded, the pulse width and/or frequency are reduced to restore an acceptable side effect level, and the process continues to step 607 and the titration session is concluded. In some embodiments, the conclusion of the titration session represented in step 607 indicates an intermediate hold has been reached. A new titration session could then be initiated after visiting a physician to release the intermediate hold.

At decision step 614, if the target pulse width and target frequency have been achieved before the maximum tolerable side effects have been exceeded, all of the stimulation parameters will have reached their target levels and the titration process concludes at step 615. The stimulation therapy may proceed with the maintenance dose at the target stimulation levels. In some embodiments, the target frequency and duty cycle achieved are for a given titration session with an intermediate hold. In this case, the patient would visit a health care provider or physician for an evaluation. The physician would then release the hold on the titration processes or initiate the beginning of therapy.

In some embodiments, in step 604, instead of reducing the frequency in order to facilitate increase of the output current, the pulse width may be reduced. For example, embodiments where the target pulse width is 250 µsec, the pulse width may be reduced, e.g., to 150 µsec or less. Then, the method proceeds to step 605, in which the output current is gradually increased again at the reduced pulse width level until the stimulation results in an intolerable side effect level or the target output current (e.g., 2.5 mA) is reached.

Therapy can also be autonomously titrated by the neurostimulator 12 in which titration progressively occurs in a self-paced, self-monitored fashion. The progression of titration sessions may occur on an autonomous schedule or may be initiated upon receipt of an input from the patient. Ordinarily, the patient 10 is expected to visit his healthcare provider to have the stimulation parameters stored by the neurostimulator 12 in the recordable memory 29 reprogrammed using an external programmer. Alternatively, the neurostimulator 12 can be programmed to automatically titrate therapy by up titrating the VNS through periodic incremental increases using titration sessions as described above. The titration process 600 will continue until the ultimate therapeutic goal is reached.

Following the titration period, therapeutic VNS, as parametrically defined by the maintenance dose operating mode, is delivered to at least one of the vagus nerves. The stimulation system 11 delivers electrical therapeutic stimulation to the cervical vagus nerve of a patient 10 in a manner that results in creation and propagation (in both afferent and efferent directions) of action potentials within neuronal fibers of either the left or right vagus nerve independent of cardiac cycle.

FIG. 7A is a simplified block diagram of an implanted neurostimulation system 700, according to an example embodiment. The implanted neurostimulation system 700 comprises a control system 702 comprising a processor programmed to operate the system 700, a memory 703, an optional physiological sensor 704, and a stimulation subsystem 706. The physiological sensor 704 may be configured to monitor any of a variety of patient physiological signals, and the stimulation subsystem 706 may be configured to deliver a stimulation signal to the patient. In one example, the physiological sensor 704 comprises an ECG sensor or an accelerometer for monitoring heart rate and/or various other physiological measurements, and the stimulation subsystem 706 comprises a neurostimulator 12 programmed to deliver ON-OFF cycles of stimulation to the patient's vagus nerve. In other examples, the physiological sensor 704 may comprise an accelerometer, an acoustic sensor, a voltmeter, and/or any other type of physiological sensor 704 configured to receive or detect various physiological measurements of the patient. The implanted system 700 may additionally include a patient input sensor 705, described in more detail below.

The control system 702 is programmed to activate the neurostimulator 12 to deliver stimulation signals at varying stimulation intensities to the patient and to monitor the physiological signals in response to those delivered stimulation signals.

The external programmer 707 shown in FIG. 7A may be utilized by a clinician or by the patient for communicating with the implanted system 700 to adjust parameters, activate therapy, retrieve data collected by the system 700, or provide other input to the system 700. In some embodiments, the external programmer 707 may be used remotely from the implanted system 700 (e.g., when the patient is not at a clinic). For example, instead of the patient coming into the clinic for a check-up during a titration hold, the clinician may check on the patient remotely (e.g., phone call, video call, etc.). The clinician could then use the external programmer 707 to activate the next titration session or modify parameters of the titration. In some embodiments, the external programmer 707 may provide an alert indicating the patient has reached a titration hold and/or that a defibrillation shock has been detected. In some embodiments, the patient receives an alert indicating a titration hold has been reached and/or that a defibrillation shock has been detected (e.g., email, text message, etc.). In some such embodiments, the external programmer 707 may include communication circuitry adapted to communicate over a long distance using one or more protocols (e.g., cellular, Internet, etc.). In some embodiments, the external programmer 707 may be configured to program the implanted system 700 with a prescribed time or window of time during which titration sessions may be initiated. This can be used, for example, to prevent a titration session from occurring at night when the patient's sleep is likely to be disturbed by the increase in stimulation intensity and resulting side effects.

Patient inputs to the implanted system 700 may be provided in a variety of ways. The implanted system 700 may include a patient input sensor 705. As described above, a patient magnet 730 may be used to provide external input to the system 700. When the patient magnet 730 is placed on the patient's chest in close proximity to the implanted system 700, the patient input sensor 705 will detect the presence of the magnetic field generated by the patient magnet 730 and provide a control input to the control system 702. For example, in some instances, after the patient receives an alert indicating that a defibrillation shock has been detected, the patient may confirm that a defibrillation shock has occurred by performing a confirmation magnet swipe. In some instances, the confirmation magnet swipe may comprise a different pattern than other types of magnet swipes (e.g., held for a longer or shorter duration). The system 700 may be programmed to receive patient inputs to set the time of day during which titration sessions are to be initiated.

In other embodiments, the patient input sensor 705 may comprise a motion sensor, such as an accelerometer, which is configured to detect tapping on the surface of the patient's chest. The patient may use finger taps in one or more predetermined patterns to provide control inputs to the implanted system 700. For example, when the motion sensor detects three rapid taps to the patient's chest, that may trigger an operation on the implanted system 700 (e.g., to initiate a titration session). Alternatively, if the motion sensor detects a predetermined pattern of taps during a titration session, the implanted system 700 will interpret those taps as a patient input indicating that the patient's tolerance zone boundary has been exceeded.

In other embodiments, the patient input sensor 705 may comprise an acoustic transducer or other sensor configured to detect acoustic signals. The system 700 may be programmed to interpret the detection of certain sounds as patient inputs. For example, the patient may utilize an electronic device, such as a smartphone or other portable audio device, to generate one or more predetermined sequences of tones. The system 700 may be programmed to interpret each of these sequences of tones as a different patient input.

The titration of the stimulation signal delivery and the monitoring of the patient's physiological response (e.g., heart rate) may be advantageously implemented using a control system 702 in communication with both the stimulation subsystem 706 and the physiological sensor 704, such as by incorporating all of these components into a single implantable device 700. In accordance with other embodiments, an external control system 712 may be implemented in a separate implanted device or in an external programmer 720 or other external device, as shown in FIG. 7B to provide control over and communication with an implanted physiological sensor 714 and a stimulation subsystem 716 similar to those describe with regard to FIG. 7A. The external programmer 720 in FIG. 7B may be utilized by a clinician or by the patient for adjusting stimulation parameters. The external programmer 720 may be in wireless communication with the implanted medical device 710, which includes the stimulation subsystem 716 and a memory 713. In the illustrated embodiment, the physiological sensor 714 is incorporated into the implanted medical device 710, but in other embodiments, the sensor 714 may be incorporated into a separate implanted device, may be provided externally and in communication with the external programmer 720, or may be provided as part of the external programmer 720. When monitoring the patients, the physician uses the external programmer 707 to connect with the implanted medical device 710. However, in some implementations, the physician must manually connect the external programmer 707 to each implanted medical device 710 to perform titration functions (e.g., change parameter settings, titration holds and settings, etc.), which can be burdensome on physicians, as well as the clinic.

Figure 8:
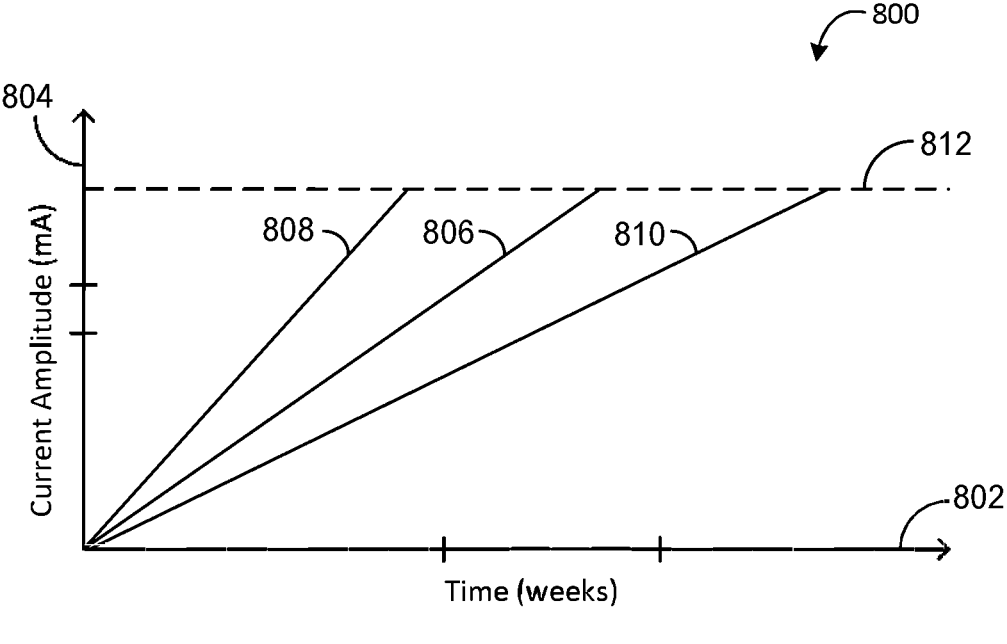
FIG. 8 is a patient titration graph illustrating different titration aggressiveness profiles, according to an example embodiment.

FIG. 8 is a patient titration graph 800 illustrating different titration aggressiveness profiles, according to an example embodiment. The graph 800 includes an x-axis 802 and a y-axis 804. The x-axis 802 is a unit of time (e.g., days, weeks, months, etc.), while the y-axis 804 is a parameter of stimulation (e.g., amplitude, frequency, duty cycle, etc.). In various embodiments, the titration graph 800 may be incorporated in a user interface displayed to a physician (e.g., on the external programmer 40 or other computing device) during the titration configuration process. The aggressiveness profiles shown in graph 800 are a medium aggressiveness profile 806, a high aggressiveness profile 808, and a low aggressiveness profile 810. Each of the aggressiveness profiles 806, 808, and 810 is associated with a rate of titration (e.g., an increment value between initial stimulation parameters and a target value 812), where the rate of titration for the high aggressiveness profile 808 is greater than the rate of titration for the medium aggressiveness profile 806, which in turn is greater than the rate of titration for the low aggressiveness profile 810. Accordingly, patients using the high aggressiveness profile 808 transition to a target value 812 from initial stimulation parameters for within a shortest time interval (e.g., 30 days), while patients using the low aggressiveness profile 810 transition to the target value 812 from initial stimulation parameters within a longest time interval (e.g., 60 days), and patients using the medium aggressiveness profile 806 transition to the target value 812 from initial stimulation parameters within an interval sometime in between the high aggressiveness profile 808 and the low aggressiveness profile 810 (e.g., 45 days). Alternatively, or additionally, the low aggressiveness profile 810, the medium aggressiveness profile 806, and the high aggressiveness profile 808 may be associated with increasingly greater target intensity values.

With each profile 806, 808, and 810, at least one stimulation parameter (e.g., stimulation current amplitude, pulse width, frequency, duty cycle, etc.) is increased (e.g., gradually increased) according to the rate of titration of the profile 806, 808, or 810. In some embodiments, the rate of titration may be linear and continuous for each of the aggressiveness profiles 806, 808, and 810, as shown in FIG. 8. In other embodiments, each rate of titration may instead be implemented as a step function where, e.g., the high aggressiveness profile 808 includes steps that are the closest together in time and the low aggressiveness profile 810 includes steps that are the furthest apart in time. For example, the titration may occur according to a fixed time interval during the daytime hours, where the number of steps implemented during that fixed time interval depends on which profile 806, 808, or 810 is used.

The profiles 806, 808, and 810 may also be linear, or the profiles 806, 808, and 810 may be non-linear (e.g., incorporating a dwell period or steeper after the stimulation amplitude exceeds a threshold after which intolerance is less likely, such as 2.0 mA). Additionally, in certain embodiments, the shape, step frequency, step sizes, etc. of the profiles 806, 808, and 810 may depend on which stimulation parameter is being increased according to the profile. For example, for the medium aggressiveness profile 806 where a final stimulation with a current amplitude of 3.5 mA, a frequency of 20 Hz, and a pulse width of 500 μs is desired, the profile 806 may include steps of 0.125 mA increments for current amplitude, 0.2 Hz for frequency, and 30 μs for pulse width. If the profiles 806, 808, and 810 are step functions, at each step the increase amount and type of the stimulation increase is determined by the trajectory of the profile 806, 808, and 810. As an example, at each step, amplitude, pulse width, and frequency may all increase, only one or two parameters may increase, or none of the parameters may increase depending on the trajectory of the profile 806, 808, and 810 according to which the stimulation is being delivered. Together, the steps for each of the stimulation parameters create a titration curve with a smooth increase in intensity.

In various embodiments, the profiles 806, 808, and 810 have the same shape and only differ on the scale of the titration. For example, the profiles 806, 808, and 810 are each stepwise functions using the same sizes of steps. The profiles 806, 808, and 810 instead differ based on how much time is allowed to pass between moving to the next step. Accordingly, the steps of the high aggressiveness profile 808 are closer together (e.g. more compressed) than the medium aggressiveness profile 806, which in turn has steps that are closer together than the low aggressiveness profile 810. However, in other embodiments, the profiles 806, 808, and 810 may instead have differently sized and/or spaced steps, the profiles 806, 808, and 810 may have different shapes, and so on. Additionally, in certain embodiments, the profiles 806, 808, and 810 may implement the same titration for a certain period of time (e.g., a standardized portion of the titration) and then branch out into their different, respective titration aggressiveness functions, for example, after a certain stimulation intensity threshold is reached.

For VNS systems 11 implementing different titration aggressiveness profiles, such as shown in graph 800, the physician inputs the final stimulation parameters that the titration is designed to reach, and the default titration profile for reaching those parameters is the medium aggressiveness profile 806. The medium aggressiveness profile 806 may be the factory-adjustable default for the VNS system 11, or the medium aggressiveness profile 806 may be the recommended profile for the physician to select (e.g., via the programmer 40) for the titration. The physician may then be able to customize the stimulation for the patient. For example, the physician may modify the duty cycle from the default (e.g., 14 seconds ON, 66 seconds OFF, with an amplitude ramp up at the beginning of each cycle and an amplitude ramp down at the end of each cycle), after which the duty cycle will be constant during the titration unless modified again by the physician.

Once the VNS system 11 is thus initialized, stimulation will occur according to the medium aggressiveness profile 806. However, if the patient experiences unwanted side effects as the titration progresses, the patient can provide a feedback signal indicating that the patient is experiencing unwanted side effects to the VNS system 11, for example, via the patient magnet 730. Those of skill in the art will appreciate, however, that while reference is made herein to the patient magnet 730, the patient may be able to signal unwanted side effects to the VNS system 11 through another mechanism, such as by an external patient programmer. Once the patient signals to the VNS system 11 that the patient is experiencing unwanted side effects, the VNS system 11 modifies the titration accordingly. The VNS system 11 may also transmit, via an implantable pulse generator (e.g., the neurostimulator 12), a receipt of the feedback signal to an external device.

In one embodiment, if the patient places the patient magnet 730 over the implanted system 700 for at least 10 seconds but less than 60 seconds, the implanted system 700 automatically decrements the stimulation intensity along the profile 806, 808, or 810 being used for the patient. If the titration is decremented three times, the implanted system 700 automatically switches the patient to a less aggressive titration profile, if possible. For example, the implanted system 700 switches the patient from the high aggressiveness profile 808 to the medium aggressiveness profile 806 or switches the patient from the medium aggressiveness profile 806 to the low aggressiveness profile 810. In switching to a less aggressive titration profile, the implanted system 700 identifies and moves to a location on the less aggressive titration profile that has a stimulation intensity less than or equal to the stimulation intensity currently being used on the current profile. As an example, the implanted system 700 moves to the highest location on the less aggressive titration profile that has a amplitude, frequency, and pulse width less than or equal to the amplitude, frequency, and pulse width currently being applied to the patient according to the more aggressive titration profile. Alternatively, if the patient places the patient magnet 730 over the implanted system 700 for at least 60 seconds, the implanted system 700 inhibits stimulation until the patient magnet 730 is removed. Once the patient magnet 730 is removed, stimulation resumes, and the stimulation intensity is not decremented. In some arrangements, if the patient uses the patient magnet 730 to decrement the stimulation intensity, move to a less aggressive profile, and/or pause the stimulation, the implanted system 700 keeps a record of the magnet activation.

Alternatively, in another embodiment, the patient informs the physician that the patient has experienced unwanted side effects, and the physician can switch the patient to a less aggressive titration profile in response to the patient feedback. Alternatively, if the patient is experiencing no side effects, the physician can switch the patient to a more aggressive profile (e.g., from the low aggressiveness profile 810 to the medium aggressiveness profile 806 or from the medium aggressiveness profile 806 to the high aggressiveness profile 808). The physician may be able to switch the profiles in person and/or remotely.

In some arrangements, once the patient is switched from a higher aggressiveness profile to a lower aggressiveness profile, the patient cannot be switched back to the higher aggressiveness profile. Conversely, in other arrangements, the patient may be switched back to a higher aggressiveness profile (e.g., either automatically by the VNS system 11 or by the physician using the programmer 40) if the patient experiences no further subsequent side effects. Additionally, in various embodiments, the VNS system 11 keeps a record of the timing of all stimulation parameter changes throughout the titration period. The log includes a record of, e.g., the timing and duration of all magnet 730 activations and can be downloaded from the implanted system 700 for viewing by the physician.

Additionally, those of skill in the art will appreciate that graph 800 is merely exemplary of different aggressiveness profiles. A VNS system 11 may implement additional or fewer aggressiveness profiles. For example, a VNS system 11 may be adapted to implement a titration aggressiveness profile that is even less aggressive than the low aggressiveness profile 810. Thus, after being moved from the medium aggressiveness profile 806 to the low aggressiveness profile 810, a patient may indicate to the VNS system 11 (e.g., via the patient magnet 730) that the patient is still experiencing adverse side effects with the low aggressiveness profile 810. Accordingly, the VNS system 11 may modify the neurostimulation signal to conform to the even less aggressive titration profile, deliver the modified neurostimulation signal, and titrate (e.g., gradually increase) the neurostimulation according to the even less aggressive titration profile.

FIG. 9 is a flowchart of a titration process 900 (e.g., implemented by the VNS system 11) including different titration aggressiveness profiles, according to an example embodiment. First, the VNS system 11 delivers a neurostimulation signal in conformance with a first titration aggressiveness profile at 902. For example, the first titration aggressiveness profile may be the medium aggressiveness profile 806 shown in FIG. 8. Next, the VNS system 11 increases at least one parameter of the first titration aggressiveness profile (e.g., output current, frequency, pulse width, or duty cycle) towards a target value (e.g., the target value 812) at 904. The VNS system 11 then receives a feedback signal from the patient indicating adverse effects from the neurostimulation signal at 906. The patient may provide the feedback signal to the VNS system 11 via a patient magnet, as described above, or through any other feedback mechanism, such as by an external patient programmer. In response to the feedback signal, the VNS system 11 modifies the neurostimulation signal to conform with a second titration aggressiveness profile at 908. For example, as discussed above, the VNS system 11 may modify the neurostimulation signal to match the low aggressiveness profile 810 shown in FIG. 8. The VNS system 11 delivers the neurostimulation signal with the second titration aggressiveness profile at 910.

The VNS system 11 then increases at least one parameter of the second titration aggressiveness profile towards the target value at 912.

As described above, stimulation may be applied by the VNS system 11 according to a duty cycle, where the duty cycle includes an ON period, an OFF period, an amplitude ramp up at the beginning of each cycle, and an amplitude ramp down at the end of each cycle. Accordingly, in many situations, it would be beneficial for the physician in a clinic setting to be able to determine when therapy is actually being applied by the VNS system 11. As such, referring back to FIG. 3, in addition to allowing the physician to interrogate the neurostimulator 12 and set parameters, the external programmer 40 may indicate to the user whether the VNS system 11 is currently delivering therapy to the patient (e.g., the "therapy active" status) based on interrogation of the neurostimulator 12. In various embodiments, the external programmer 40 may display the therapy active status on the visual display 44 of the programming computer 41. For example, in one embodiment, the visual display 44 may include an on-off therapy status indicator and show via the indicator whether the neurostimulator 12 is ON or OFF. In another embodiment, in response to an interrogation of the neurostimulator 12, the external programmer 40 may display a countdown time to the next stimulation burst.

The external programmer 40 may display the therapy active status in real time. Alternatively, the external programmer 40 may display the therapy active status asynchronously from the interrogation response from the neurostimulator 12 such that the external programmer 40 accounts for the transport delay between the external programmer 40 and the neurostimulator 12 and the display of the therapy active status coincides with the stimulation burst being applied to the patient. In another arrangement, when interrogating the neurostimulator 12, the external programmer 40 may query the neurostimulator 12 to receive a block of timing data that enables the programmer 40 to sync its therapy active displays to the stimulation delivered by the VNS system 11. Additionally, in yet another arrangement, the external programmer 40 may display the therapy active status in real time or accounting for the transport delay while in communication with the neurostimulator 12 and also receive a block of timing data that enables the programmer 40 to continue displaying the therapy active status once communication ceases between the external programmer 40 and the neurostimulator 12.

Figure 10:
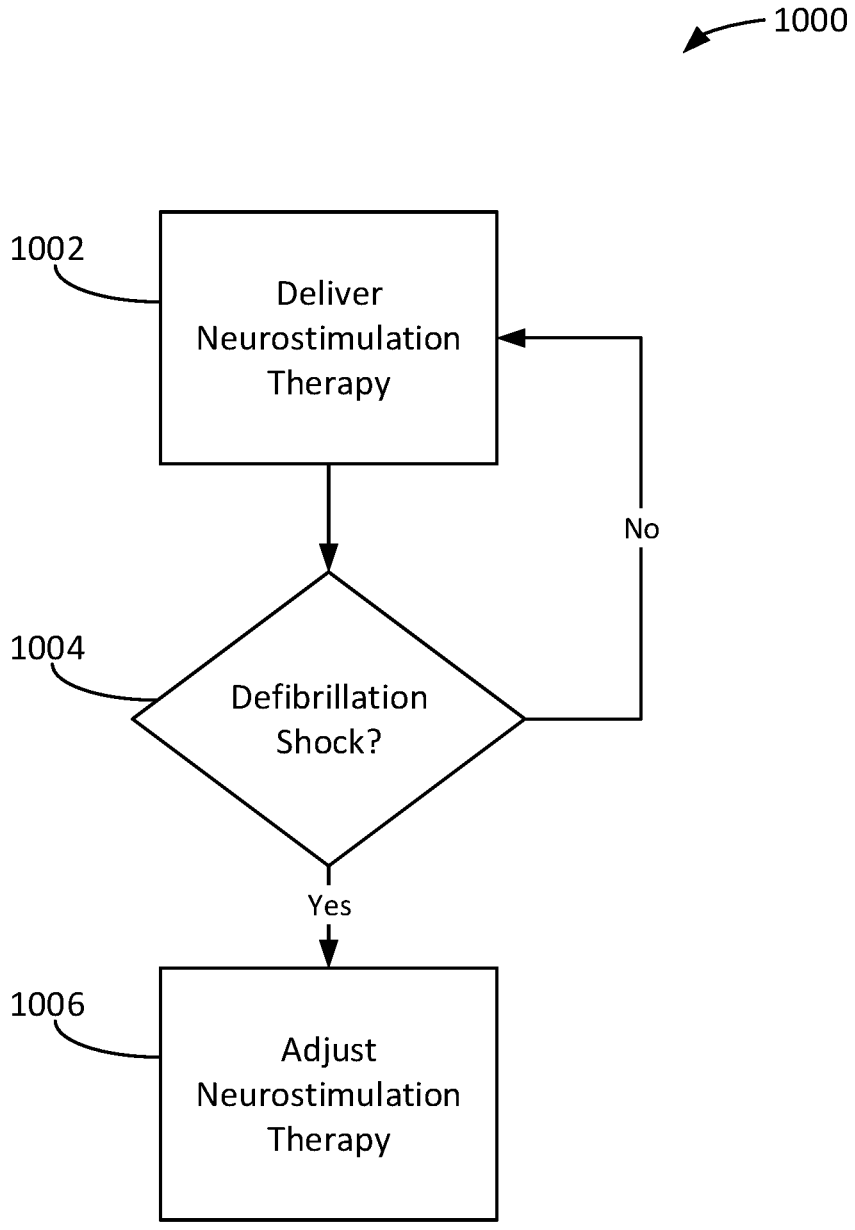
FIG. 10 is a flowchart of a neurostimulation therapy process that includes defibrillation sensitivity compensation, according to an example embodiment.

Referring now to FIG. 10, a method 1000 for delivering neurostimulation therapy with defibrillation sensitivity compensation is shown, according to an example embodiment. Specifically, in some instances, following a cardiac defibrillation shock, patients experience an increased sensitivity to neurostimulation. Accordingly, the method 1000 allows for a neurostimulation therapy delivered to a patient (e.g., a preset neurostimulation titration scheme) to automatically account for detected cardiac defibrillation shocks received by the patient by adjusting the neurostimulation delivered to the patient.

The method 1000 begins with an implantable medical device (e.g., the implantable vagus stimulation system 11, implanted system 700, implanted medical device 710) delivering a neurostimulation therapy to a patient, at step 1002. In some instances, the implantable medical device may be configured to provide neurostimulation therapy in accordance with any of the various techniques disclosed herein. For example, the neurostimulation therapy delivered to the patient may follow any of the titration process 500, shown in FIG. 5, the titration process 600, shown in FIG. 6, or the titration process 900. In some other instances, the neurostimulation therapy may be any of a variety of other neurostimulation therapies (VNS or other types of stimulation) directed at treating or otherwise counteracting various ailments (e.g., CHF, depression, epilepsy) that may or may not be delivered to the patient using a titration scheme.

While delivering the neurostimulation therapy, at step 1002, the implantable medical device may then determine whether the patient has experienced a defibrillation shock, at step 1004. In some instances, the implantable medical device may be configured to determine that the patient has experienced the defibrillation shock in one or more of the following ways: (1) the implantable medical device receives a signal from a defibrillation device indicating that a defibrillation shock has been applied to the patient, (2) the implantable medical device receives a signal from a sensor implanted in the patient that is indicative of the patient receiving a defibrillation shock, or (3) the implantable medical device receives a patient input indicative of the patient receiving a defibrillation shock.

For example, in some instances, the implantable medical device may be in communication with an external or separate implantable defibrillation device (e.g., via a Bluetooth or other wireless communication). Accordingly, the implantable medical device may receive one or more wireless signals from the external or separate implantable defibrillation device indicating that a defibrillation shock has been provided to the patient. In some other instances, the implantable medical device may, in addition to a stimulation subsystem (e.g., stimulation subsystem 706, stimulation subsystem 716), include a cardiac defibrillation subsystem configured to selectively apply cardiac defibrillation shocks to the patient. For example, in some instances, the implantable medical device may be a dual VNS and cardioverter-defibrillation device similar to that described in U.S. Pat. No. 9,770,599, entitled "Vagus Nerve Stimulation and Subcutaneous Defibrillation System," filed on Aug. 12, 2014, the entire contents of which are hereby incorporated by reference. In these instances, because the implantable medical device is the device applying the defibrillation shock, the controller of the implantable medical device (e.g., electronic circuitry 22, control system 702) may automatically receive an indication from the cardiac defibrillation subsystem that a defibrillation shock has been applied to the patient, or the implantable medical device may be aware that a defibrillation shock has been applied (e.g., if the same control system initiated the signal to cause the defibrillation shock to be applied).

In some other instances, the implantable medical device may alternatively be configured to determine that the patient has received the defibrillation shock based on one or more signals received from one or more sensors implanted in the patient. For example, in some instances, the implantable medical device may include one or more physiological sensors (e.g., physiological sensor 31, physiological sensor 704, physiological sensor 714) configured to sense or otherwise detect one or more measurements within the patient's body. In some other instances, the implantable medical device may be communicatively coupled to one or more separate physiological sensors via a Bluetooth, Wi-Fi, or other suitable wireless communication method.

For example, in some instances, the physiological sensors may include an electrocardiogram (EKG) sensor configured to sense an EKG signal of the patient. In these instances, the implantable medical device may be configured to detect a sudden change in the patient's EKG signal (e.g., a change in the amplitude or waveform) and associate the sudden change with the onset of a defibrillation shock.

In some instances, the implantable medical device may determine that the patient has received a defibrillation shock based on a voltage reading sensed within the patient. For example, in some instances, the physiological sensor may be configured to detect a voltage difference between two locations within the patient (e.g., via one or more electrodes and/or the housing of the implantable medical device). Accordingly, when a defibrillation shock is applied to the patient, the physiological sensor may detect an increase in the measured voltage. The implantable medical device may then determine that the patient has received the defibrillation shock based on the increased voltage measurement.

In some instances, the implantable medical device may compare the voltage measurement to a high voltage threshold and only determine that the patient has received the defibrillation shock when the voltage measurement exceeds the high voltage threshold. In some instances, the implantable medical device may further require that the measured voltage exceeds the high voltage threshold for at least a preset duration of time before determining that the patient has received a defibrillation shock. In some instances, the high voltage threshold and the preset duration of time may each be set during an initial programming of the implantable medical device.

As an example, in some instances, the high voltage threshold may be between 1 mV and 1V, between 1V and 10V, or between 10V and 100V. In some instances, the high voltage threshold may be based on a scaled-down value of an expected voltage applied by an automated external defibrillation (AED) or an implantable cardioverter-defibrillator (ICD). In some instances, this scaling down of the high voltage threshold value may be done to prevent damage to the implantable medical device. Additionally, as another example, the preset duration of time may be between 5 ms and 200 ms. For example, in some instances, an ICD shock may be delivered with a biphasic waveform where each phase lasts between 3 ms and 5 ms. Accordingly, in this instance, a preset duration of time of 5 ms may be utilized. In some other instances, the preset duration of time may be 100 ms.

It should be appreciated that the high voltage threshold and/or the preset duration of time may be dependent upon an implantation location of the one or more electrodes. As such, the high voltage threshold and/or the preset duration of time in some other embodiments may be selected for an intended implantation configuration. In any case, by setting the high voltage threshold and the preset duration of time, the detection of the defibrillation shocks may have improved resistance to false positives resulting from non-defibrillation electromagnetic interference.

In some instances, the physiological sensors may include an accelerometer configured to obtain acceleration data from the patient. For example, the acceleration data may comprise acoustic data indicative of heart sound profiles. In some instances, the implantable medical device may be configured to monitor the heart sound profiles during a normal period of neurostimulation therapy (i.e., where the patient has not received a defibrillation shock) to develop a baseline heart sound profile of the heart (e.g., a baseline S2 heart sound). This baseline heart sound profile may then be stored within the implantable medical device (e.g., with recordable memory 29, memory 703, memory 713). This baseline heart sound profile may provide a "normal acoustic energy" resulting from the patient's regular cardiac contractions. As such, the implantable medical device may be configured to monitor the acoustic data obtained from the patient via one or more accelerometers and identify whether the acoustic data is indicative of a defibrillation shock being delivered to the patient (e.g., indicative of shock-induced acoustic energy) by comparing the acoustic data to the baseline heart sound profile.

For example, in some instances, if the comparison between the obtained acoustic data and the baseline heart sound profile indicates that the obtained acoustic data is sufficiently different from the expected baseline heart sound profile, the implantable medical device is configured to determine that the patient has received a defibrillation shock. In some instances, a preselected portion of the baseline heart sound profile may be used in the aforementioned comparison for determining that the patient has received a defibrillation shock. For example, in some instances, a sudden change in the second heart sound (S2) may be utilized by the implantable medical device to determine that the patient has received a defibrillation shock. In some instances, the comparison between the baseline heart sound profile and the acoustic data may be utilized to trigger an in-depth acoustic energy analysis configured to identify whether the patient has received a defibrillation shock.

In some instances, upon the implantable medical device determining that the patient has potentially received a defibrillation shock, the implantable medical device may further require that the patient confirm the suspected defibrillation shock event. For example, in some instances, the implantable medical device, upon determining that the patient has likely received a defibrillation shock based on any of the aforementioned physiological signals, may enter a confirmation-enabled mode for a preset period of time within which the patient is able to confirm a suspected defibrillation shock.

In some instances, the patient may confirm the defibrillation shock via a magnet swipe. For example, in some instances, the patient may use a different magnet swipe (e.g., a different duration, number of swipes, or pattern of swipes) than that discussed above, with respect to magnet mode, to signal to the implantable medical device that the patient has received a defibrillation shock. In some instances, within the confirmation-enabled mode, the implantable medical device may interpret any type of magnet swipe as a confirmation of the defibrillation shock. As such, if the patient performs the magnet swipe within the confirmation-enabled mode window of time, the implantable medical device determines that the patient has confirmed the defibrillation shock. In these instances, if the patient does not perform a magnet swipe within the preset time window, the implantable medical device determines that the patient has not received a defibrillation shock (e.g., that the suspected defibrillation shock was a false positive detection).

In some other instances, upon detecting a suspected defibrillation shock, the implantable medical device may communicate with a user device (e.g., a smart phone application) of the patient via Bluetooth, Wi-Fi, or any other suitable short-range wireless communication method to provide the patient with a prompt asking the patient to confirm whether the patient received a defibrillation shock. In these instances, the patient may confirm the defibrillation shock using the user device, which may communicate this confirmation back to the implantable medical device using the Bluetooth, Wi-Fi, or other short-range wireless communication method. The patient may alternatively indicate that no defibrillation shock has been received. Accordingly, if the patient does not respond within the preset time window or responds indicating that no defibrillation shock has been received, the implantable medical device may similarly determine that the suspected defibrillation shock was a false positive detection.

In some instances, the implantable medical device is configured to allow the patient to indicate that a defibrillation shock has been received at any time (e.g., with or without a previously detected suspected defibrillation shock). That is, in some instances, the patient may perform a pre-set magnet swipe, different in length, number, and/or pattern than the magnet mode swipe discussed above, that the implantable medical device is configured to recognize as indicative of the patient receiving a defibrillation shock regardless of any previously detected defibrillation shocks. Similarly, in some instances, an application on the user device of the patient may allow the patient to indicate that the patient has received the defibrillation shock, regardless of any previously detected defibrillation shocks.

In any case, if the implantable medical device determines that the patient has not received a defibrillation shock, at step 1004, the implantable medical device continues delivering the neurostimulation therapy, as initially programmed, at step 1002. Alternatively, if the implantable medical device determines that the patient has received a defibrillation shock, at step 1004, the implantable medical device is configured to adjust the neurostimulation therapy to automatically compensate for the increased level of patient sensitivity to neurostimulation.

For example, in some instances, upon determining that the patient has received a defibrillation shock, the implantable medical device may temporarily suspend all stimulation for a predetermined period of time. That is, the implantable medical device may cease any delivery of neurostimulation applied to the patient and may hold off on delivering any subsequent neurostimulation for at least the predetermined period of time to allow for the patient to recover from the defibrillation shock without receiving additional neurostimulation. As such, in some instances, the patient may not receive any neurostimulation generally for a period of time following a defibrillation shock, thereby preventing the patient from experiencing neurostimulation-based discomfort during the period of increased sensitivity following the defibrillation shock. In some instances, the predetermined period of time may be set during an initial setup of the implantable medical device. As an example, in some instances, the predetermined period of time may be between one hour and several hours, between one day and several days, or between one week and several weeks.

In some instances, once the predetermined period of time has ended, the implantable medical device may resume titration using the same neurostimulation parameters (e.g., current amplitude, frequency, pulse width) that were being delivered prior to suspending stimulation. In some other instances, once the predetermined period of time has ended, the implantable medical device may begin titration from a reduced intensity (e.g., a reduced current amplitude, a reduced frequency, and/or a reduced pulse width).

In some other instances, upon determining that the patient has received a defibrillation shock, the implantable medical device may alternatively temporarily reduce an intensity of the neurostimulation provided to the patient for the predetermined period of time. For example, the implantable medical device may temporarily reduce the current amplitude, the frequency, and/or the pulse width for the period of time following the defibrillation shock. In some instances, the reduction of the current amplitude, the frequency, and/or the pulse width in response to the detected defibrillation shock may be larger than the reduction in the current amplitude, the frequency, and/or the pulse width that is performed in response to the implantable medical device entering the magnet mode, discussed above. While the intensity of the neurostimulation is reduced, the titration of the neurostimulation signal provided to the patient may be temporarily paused, such that the neurostimulation signal remains at the same reduced intensity for the entire predetermined period of time following the defibrillation shock.

In these instances, once the predetermined period of time has ended, the implantable medical device may similarly resume titration using the same neurostimulation parameters (e.g., current amplitude, frequency, pulse width) that were being delivered prior to reducing the stimulation intensity or may instead begin titration from the reduced intensity.

In some other instances, upon determining that the patient has received a defibrillation shock, the implantable medical device may similarly reduce an intensity of the neurostimulation provided to the patient (e.g., the current amplitude, the frequency, and/or the pulse width), but instead of maintaining the reduced stimulation intensity for a period of time, the implantable medical device may instantly begin titration from the reduced stimulation intensity. That is, upon detecting a defibrillation shock, the implantable medical device may step back the stimulation intensity and instantly begin titrating the neurostimulation signal from the lower stimulation intensity.

In any of the aforementioned scenarios, the titration of the stimulation may be resumed using the same aggressiveness profile or a less aggressive titration aggressiveness profile (e.g., similar to the titration aggressiveness profiles discussed above, with respect to FIG. 8). In some scenarios, the selection of suspending all stimulation, reducing stimulation intensity and suspending titration, or reducing stimulation intensity and instantly beginning titration from the lower stimulation intensity may be selectable options presented to the physician (e.g., via application software 45 of the external programmer 40) upon initial programming of the implantable medical device. Similarly, the physician may be able to select (e.g., via the application software 45 on the external programmer 40) the period of time for which the stimulation and/or titration is suspended and/or the parameters that are reduced, as well as the amount that each parameter is reduced upon detection of a defibrillation shock.

While embodiments been particularly shown and described, those skilled in the art will understand that the foregoing and other changes in form and detail may be made therein without departing from the spirit and scope. For example, in various embodiments described above, the stimulation is applied to the vagus nerve. Alternatively, spinal cord stimulation (SCS) may be used in place of or in addition to vagus nerve stimulation for the above-described therapies. SCS may utilize stimulating electrodes implanted in the epidural space, an electrical pulse generator implanted in the lower abdominal area or gluteal region, and conducting wires coupling the stimulating electrodes to the generator. Similarly, while the aforementioned stimulation titration is discussed largely in the context of CHF, it should be appreciated that the titration methods discussed here can be applied to a variety of alternative stimulation-based therapies, such as, for example, stimulation-based sleep apnea therapy, stimulation-based depression therapy, stimulation-based epilepsy therapy, and/or any other type of stimulation-based therapy in which titration of stimulation from a starting intensity toward a therapeutic or target intensity would be useful.

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, Z, X and Y, X and Z, Y and Z, or X, Y, and Z. Thus, such conjunctive language is not generally intended to imply that certain embodiments require at least one of X, at least one of Y, and at least one of Z to each be present.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of delivering neurostimulation therapy to a patient from an implantable medical device, the method comprising:

delivering, by the implantable medical device, the neurostimulation therapy to the patient;

determining, by the implantable medical device, that the patient has received a defibrillation shock from a defibrillation device; and adjusting, by the implantable medical device, the neurostimulation therapy based on determining that the patient has received the defibrillation shock.

2. The method of claim 1, wherein adjusting the neurostimulation therapy comprises temporarily suspending stimulation.

3. The method of claim 1, wherein adjusting the neurostimulation therapy comprises temporarily reducing a stimulation intensity of the neurostimulation therapy.

4. The method of claim 3, further comprising, subsequent to temporarily reducing the stimulation intensity, gradually increasing, by the implantable medical device, the stimulation intensity.

5. The method of claim 1, further comprising receiving, by the implantable medical device, a signal from a sensor of the implantable medical device, wherein determining that the patient has received the defibrillation shock is performed based on the signal received by the sensor.

6. The method of claim 5, wherein the sensor is an electrocardiogram sensor, and the signal received from the electrocardiogram sensor is an electrocardiogram signal.

7. The method of claim 5, wherein the sensor is configured to receive a voltage signal within the patient and determining that the patient has received the defibrillation shock is performed based on the voltage signal being above a voltage threshold for longer than a preset time duration.

8. The method of claim 5, wherein the sensor is an accelerometer configured to receive an acceleration signal and determining that the patient has received the defibrillation shock is performed based on the acceleration signal being indicative of shock-induced acoustic energy.

9. The method of claim 1, further comprising receiving, by the implantable medical device, an input signal from the patient indicating that the patient has received the defibrillation shock, wherein determining that the patient has received the defibrillation shock is performed based on the input signal.

10. The method of claim 9, wherein the input signal is received via one of a magnet swipe or a wireless communication from a user device associated with the patient.

11. The method of claim 9, wherein the implantable medical device includes the defibrillation device.

12. A method of delivering neurostimulation therapy to a patient from an implantable medical device, the method comprising:

delivering, by the implantable medical device, the neurostimulation therapy to the patient;

receiving, by the implantable medical device, a signal from a sensor of the implantable medical device;

determining, by the implantable medical device, that the patient has received a defibrillation shock from a defibrillation device based on the signal received from the sensor; and reducing, by the implantable medical device, an intensity of the neurostimulation therapy based on determining that the patient has received the defibrillation shock.

13. The method of claim 12, wherein the sensor is an electrocardiogram sensor, and the signal received from the electrocardiogram sensor is an electrocardiogram signal.

14. The method of claim 12, wherein the sensor is configured to receive a voltage signal within the patient and determining that the patient has received the defibrillation shock is performed based on the voltage signal being above a voltage threshold for longer than a preset time duration.

15. The method of claim 12, wherein the sensor is an accelerometer configured to receive an acceleration signal and determining that the patient has received the defibrillation shock is performed based on the acceleration signal being indicative of shock-induced acoustic energy.

16. An implantable medical device comprising:

at least one processing circuit including at least one processor and at least one memory, the at least one memory having instructions stored thereon that, when executed by the at least one processor, cause the at least one processor to perform operations comprising:

delivering neurostimulation therapy to a patient;

determining that the patient has received a defibrillation shock from a defibrillation device; and adjusting the neurostimulation therapy based on determining that the patient has received the defibrillation shock.

17. The implantable medical device of claim 16, wherein adjusting the neurostimulation therapy comprises:

temporarily reducing a stimulation intensity of the neurostimulation therapy; and subsequent to temporarily reducing the stimulation intensity, increasing the stimulation intensity.

18. The implantable medical device of claim 16, further comprising a sensor configured to receive a signal, wherein the operations further comprise receiving the signal from the sensor, and wherein determining that the patient has received the defibrillation shock is performed based on the signal received by the sensor.

19. The implantable medical device of claim 18, wherein the sensor is one of an electrocardiogram sensor, a voltage sensor, or an accelerometer.

20. The implantable medical device of claim 16, wherein the operations further comprise receiving an input signal from the patient indicating that the patient has received the defibrillation shock, the input signal received via one of a magnet swipe or a wireless communication from a user device associated with the patient, and wherein determining that the patient has received the defibrillation shock is performed based on the input signal.

\* \* \* \* \*